Figure 1:
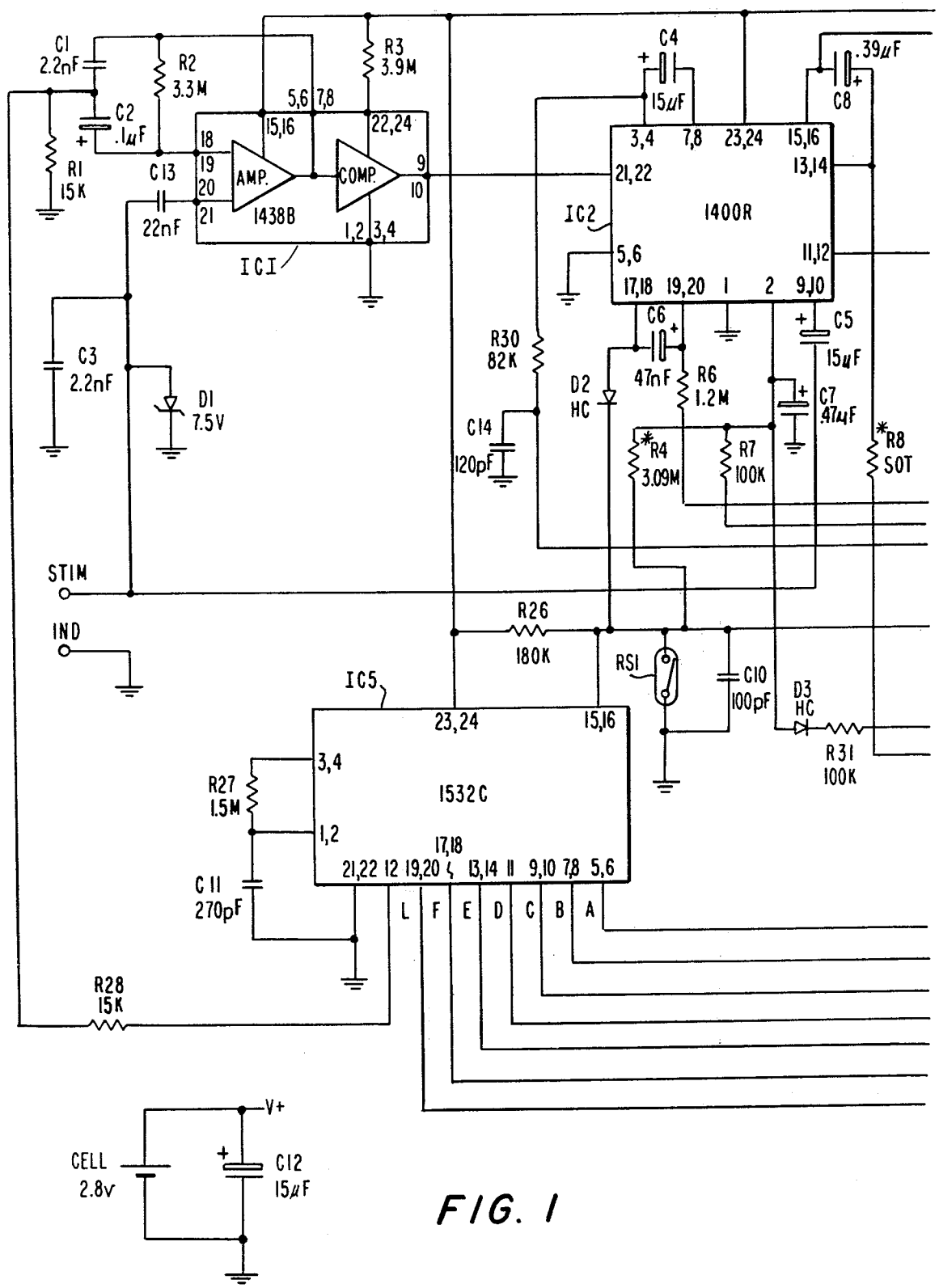

United States Patent [19]

Spurrell et al.

[11] 4,427,011
[45] Jan. 24, 1984

[54] TACHYCARDIA CONTROL PACER WITH IMPROVED DETECTION OF TACHYCARDIA TERMINATION

[75] Inventors: Roworth A. J. Spurrell, London, England; Tibor A. Nappholz, Drummoyne; Stephen J. Swift, Hornsby, both of Australia

[73] Assignee: Telectronics Pty. Ltd., Lane Cove, Australia

[21] Appl. No.: 359,364

[22] Filed: Mar. 18, 1982

[51] Int. Cl.³ .............................................. A61N 1/36
[52] U.S. Cl. ........................ 128/419 PG; 128/419 D; 128/705
[58] Field of Search ..... 128/419 PG, 419 D, 705–706

[56] References Cited

U.S. PATENT DOCUMENTS

| | | |
|---|---|---|
| 3,693,627 | 9/1972 | Berkovits ...................... 128/419 PG |
| 3,698,398 | 10/1972 | Berkovits ...................... 128/419 PG |
| 3,805,796 | 4/1974 | Terry, Jr. et al. ............ 128/419 PG |
| 3,939,844 | 2/1976 | Pequignot ...................... 128/419 PG |
| 3,942,534 | 3/1976 | Allen et al. .................... 128/419 PG |
| 4,163,451 | 8/1979 | Lesnick et al. ................. 128/419 PG |
| 4,181,133 | 1/1980 | Kolenik et al. ................ 128/419 PG |
| 4,280,502 | 7/1981 | Baker, Jr. et al. ............. 128/419 PG |
| 4,307,725 | 12/1981 | Sowton et al. ................. 128/419 PG |
| 4,312,356 | 1/1982 | Sowton et al. ................. 128/419 PG |
| 4,390,021 | 6/1983 | Spurrell et al. ............... 128/419 PG |
| 4,398,536 | 8/1983 | Nappholz et al. ........... 128/419 PG |

FOREIGN PATENT DOCUMENTS 826766  1/1960  United Kingdom ......... 128/419 PG

OTHER PUBLICATIONS

"Implantable Automatic Scanning Pacemaker for Termination of Supraventricular Tachycardia" Spurrell et al., *Am. J. Cardiology*, vol. 49, Mar. 1982 pp. 753–760.

*Primary Examiner*—William E. Kamm
*Assistant Examiner*—Mitchell J. Shein
*Attorney, Agent, or Firm*—Gottlieb, Rackman & Reisman

[57] ABSTRACT

A tachycardia control pacer in which at least one scanned pulse is generated following each tachycardia confirmation, and the last-used pulse timing is retained following the next tachycardia termination for subsequent first use following the next tachycardia confirmation. The tachycardia termination detecting circuit does not respond to the time interval between at least the first two heartbeats following a generated pulse, to prevent a false determination of tachycardia termination due to the excessive pauses which sometimes occur immediately after pacing despite the fact that tachycardia has not terminated.

18 Claims, 19 Drawing Figures

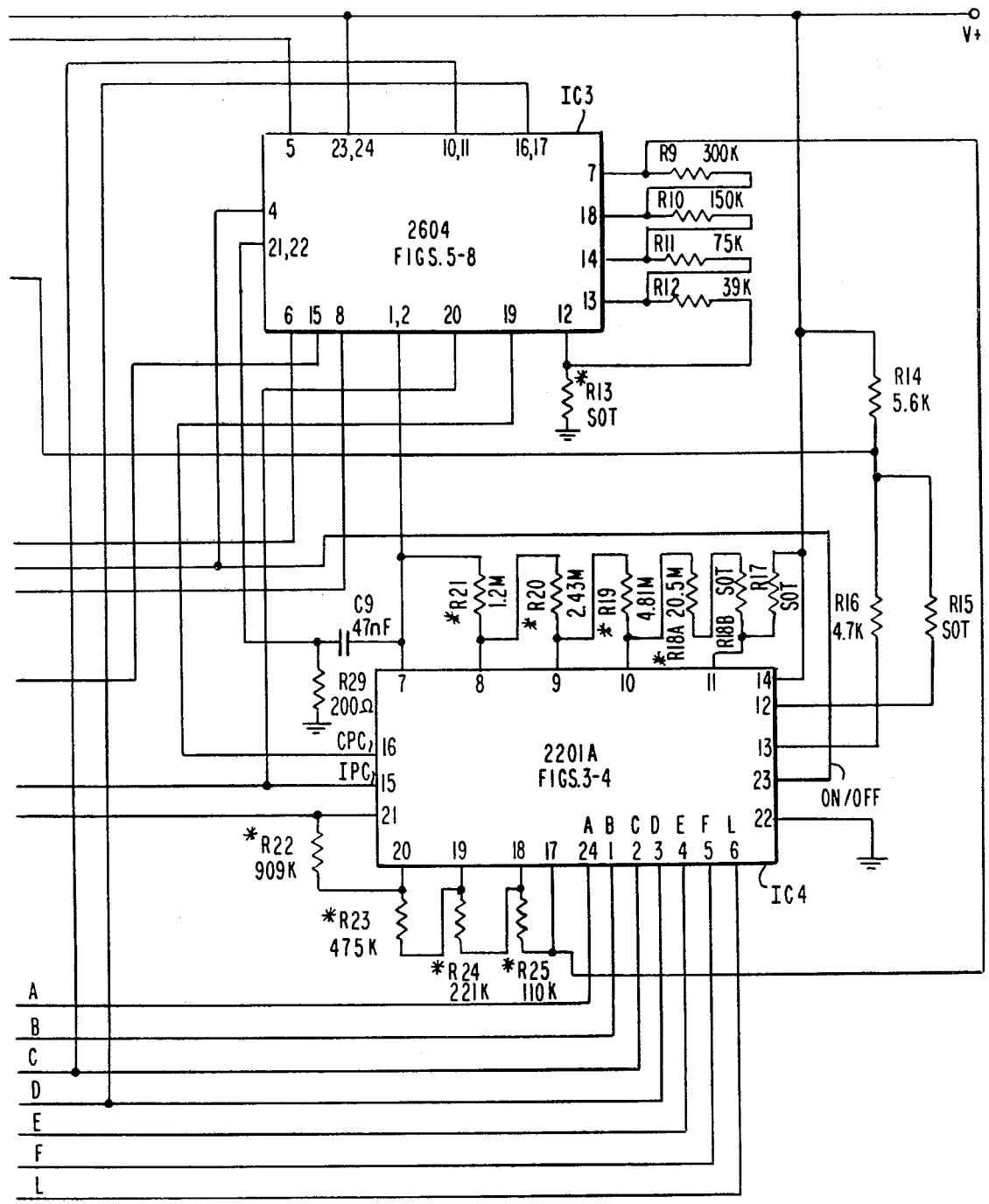
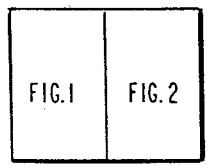
FIG. 2
FIG. 2A

TACHYCARDIA CONTROL PACER WITH IMPROVED DETECTION OF TACHYCARDIA TERMINATION

DESCRIPTION

This invention relates to tachycardia control pacers, and more particularly to improved detection of tachycardia termination.

Tachycardia is a condition in which the heart beats very rapidly, typically, above 150 beats per minute. There are several different pacing modalities which have been suggested for termination of tachycardia. The underlying principle in all of them is that if a pacer stimulates the heart at least once shortly after a heartbeat, before the next naturally occurring heartbeat at the rapid rate, the heart may successfully revert to sinus rhythm. Tachycardia is often the result of electrical feedback within the heart; a natural beat results in the feedback of an electrical stimulus which prematurely triggers another beat. By interposing a stimulated heartbeat, the stability of the feedback loop is disrupted. As with conventional heart pacers, the electrodes of a tachycardia control pacer may be atrially-coupled or ventricularly-coupled. Although the detection of atrial beats and atrial stimulation are preferred, ventricular beat detection and pacing may also be employed.

The difficulty in tachycardia control is that there is usually no way of knowing exactly when a stimulating pulse should be applied. It must be applied shortly after a heartbeat and prior to the time when the next premature beat would otherwise occur, but there is usually only a short period of time somewhere between successive beats during which the generation of a stimulating pulse will successfully terminate tachycardia. This "region of susceptibility" varies not only from patient to patient, but from day to day with the same patient as well. For any given patient on any given day, the "region of susceptibility" within the overall tachycardia cycle is relative short and it may actually vary even during a single episode of tachycardia. (The term "region of susceptibility" refers to the fact that if the "re-entry" circuit in the heart, the feedback path, is disrupted during a "susceptible" time "region", successful reversion may be achieved.)

In Spurrell-Allen-Kenny U.S. Pat. No. 3,942,534, entitled "Device for Terminating Tachycardia" and issued on Mar. 9, 1976 (corresponding to British Pat. No. 1,493,353 dated Nov. 30, 1977), there is disclosed a pacer which, following detection of tachycardia, generates a stimulus after a delay interval. If that stimulus is not successful in terminating the condition, then another stimulus is generated after another premature heartbeat following a slightly different delay. The device constantly adjusts the delay interval by "scanning" through a predetermined delay range. Stimulation ceases as soon as the heart is restored to sinus rhythm. If successful reversion is not achieved during one complete scan, then the cycle is repeated.

The above-identified Spurrell et al patent further teaches the generation of a second stimulus following the first, both stimuli occurring within the tachycardia cycle, i.e., before the next naturally occurring rapid beat. It has actually been found that the second stimulus may be more effective than the first. As used herein, the time period between a heartbeat and the first stimulus is referred to as the "initial delay", and the time period between the first stimulus and the second stimulus is referred to as the "coupled interval". In the Spurrell et al device, although the coupled interval may be set by the physician, it is fixed once it is set; the second stimulus always occurs a predetermined time after the first stimulus, no matter when the first stimulus occurs after the last heartbeat.

In the Spurrell et al prior art pacer, the initial delay is controlled by the charge on a capacitor. During scanning of the initial delay, the capacitor charge is changed in discrete steps. After a successful reversion the capacitor charge dissipates slowly so that should another tachycardia episode occur soon, the scanning begins with an initial delay which is close to that which was successful in terminating the condition the last time. However, if another episode occurs long after the successful reversion, the scanning begins at one of its extremes.

In copending applications entitled "Two-Pulse Tachycardia Control Pacer", Ser. No. 245,215 filed on Mar. 19, 1981, and "Externally-Reset Tachycardia Control Pacer", Ser. No. 245,356 filed on Mar. 19, 1981 which applications are hereby incorporated by reference, there is disclosed a tachycardia control pacer in which the time intervals which are successful in terminating tachycardia are maintained so that, no matter when the next tachycardia episode occurs, the scanning begins with the most recent successful time parameters. While this is no guarantee that the first pair of stimuli will necessarily result in successful tachycardia termination, on average it takes many fewer stimuli to achieve successful reversion because the scanning always begins with the last successful time parameters.

Unlike the pacer disclosed in the above-identified Spurrell et al U.S. Pat. No. 3,942,534, in which it is only the initial delay which is scanned (with the coupled interval being fixed and the second stimulus always occurring at a predetermined time after the first stimulus), in the pacer disclosed in our copending application the coupled interval is scanned as well as the initial delay, and the successful coupled interval is registered together with the successful initial delay so that the two retained parameter values may be used first when the next tachycardia episode is detected. This gives rise to an even greater likelihood of a successful reversion with the first pair of stimuli the next time they are required.

As mentioned above, there are several different pacing modalities which have been suggested for termination of tachycardia. In addition to those described in Spurrell et al U.S. Pat. No. 3,942,534 and our above-identified copending application, three other efficacious pacing schemes are disclosed in the copending applications of Nappholz et al, entitled "Scanning Burst Tachycardia Control Pacer", Ser. No. 284,349, filed on July 17, 1981; Nappholz et al, entitled "Variable Length Scanning Burst Tachycardia Control Pacer", Ser. No. 284,348, filed on July 17, 1981; and Spurrell et al, entitled "Rate-Related Tachycardia Control Pacer", Ser. No. 245,216, filed on Mar. 6, 1981; all of which applications are hereby incorporated by reference. Although the pacing sequences in all of these tachycardia control pacers are different, they all have one thing in common, and that is the need to detect whether tachycardia has terminated. If it has not, then the patient's heart must be paced once again; if it has, further pacing is not required and, in a case where successful time parameter values must be maintained, these values should be registered for subsequent use following the next tachycardia confirmation. Although our invention is described in the context of the pacer described in our copending application, it is to be understood that the problem toward which our invention is directed and its solution are equally applicable to other types of tachycardia control pacers.

In the pacer disclosed in our copending application, following the generation of a pacing pulse sequence, heart activity is sensed to detect whether tachycardia has terminated. The time interval between the next two heartbeats is measured, and if this time interval exceeds a predetermined value the pacer assumes that tachycardia has terminated. This same time interval is used to confirm tachycardia when it is present; if five successive heartbeats are detected separated by intervals each of which is less than the predetermined value, then tachycardia is confirmed and a pacing sequence ensues. The reciprocal of the predetermined time period is referred to as the "tachy" rate.

It has been found that the pacer disclosed in our copending application on occasion determines that tachycardia has terminated when in fact it has not. Although the pacer soon confirms tachycardia once again, by sensing that each of four successive inter-beat intervals is less than the reciprocal of the tachy rate, because of the "false" prior determination that tachycardia had terminated, the pacer assumes that the last-used time parameter values were successful and it uses them at the start of the next scanning sequence. If the pacer once again falsely determines that tachycardia has terminated, this gives rise to use of the same time parameter values—values which were not successful. This problem of false determination of tachycardia termination following the generation of a pacing sequence is not unique to the pacer disclosed in our copending application, and is in fact generally present in tachycardia control pacers having different modalities.

It is a general object of our invention to provide an improved mechanism for detecting tachycardia termination in a tachycardia control pacer.

In the pacer disclosed in our copending application, the system takes no action based upon the time interval between the last generated stimulating pulse and the first heartbeat which is sensed thereafter. To determine whether tachycardia has terminated, the system measures the time interval between the first and second heartbeats, or any successive pair, to see if it is longer than the reciprocal of the tachy rate. We have discovered that on occasion there is a long compensatory pause, not only between the last generated pacing pulse and the first sensed heartbeat, but also between the first and second heartbeats which occur following conclusion of the pacing sequence. This interval is sometimes longer than the reciprocal of the tachy rate, with only the inter-beat intervals starting with the second heartbeat being shorter than the reciprocal of the tachy rate when tachycardia has indeed not been terminated. Although tachycardia persists, the single compensatory pause between the first two heartbeats results in an erroneous determination of successful reversion.

In accordance with the principles of our invention, the pacer ignores not only the time interval between the last generated pacing pulse and the first heartbeat which occurs thereafter, but also the inter-beat interval between this first heartbeat and the next one. In this way, the compensatory pause which may be present even though tachycardia persists does not give rise to an erroneous determination that the patient's heart is now beating in sinus rhythm. It is the time intervals between heartbeats, starting with the second heartbeat after pacing, that are measured to determine whether tachycardia has terminated. If a number of successive inter-beat intervals following the second heartbeat are all too low in value, then the system determines that tachycardia has not terminated and another pacing pulse sequence is generated. On the other hand, if any one of these inter-beat intervals exceeds the reciprocal of the tachy rate, then the system assumes that tachycardia has been terminated. By ignoring the first inter-beat interval altogether, the pacer is much less susceptible to falsely detecting that the condition has been successfully treated. (It is to be appreciated that instead of ignoring just the first inter-beat interval, two or more such intervals can be ignored since in some cases several compensatory pauses may be present following the generation of a pulse sequence. However, the greater the number of inter-beat intervals which are ignored, the longer it takes to confirm tachycardia. While we prefer to ignore only the first inter-beat interval, a tachycardia control pacer can be provided which ignores more than one interval depending upon patient needs.)

Figure 3:
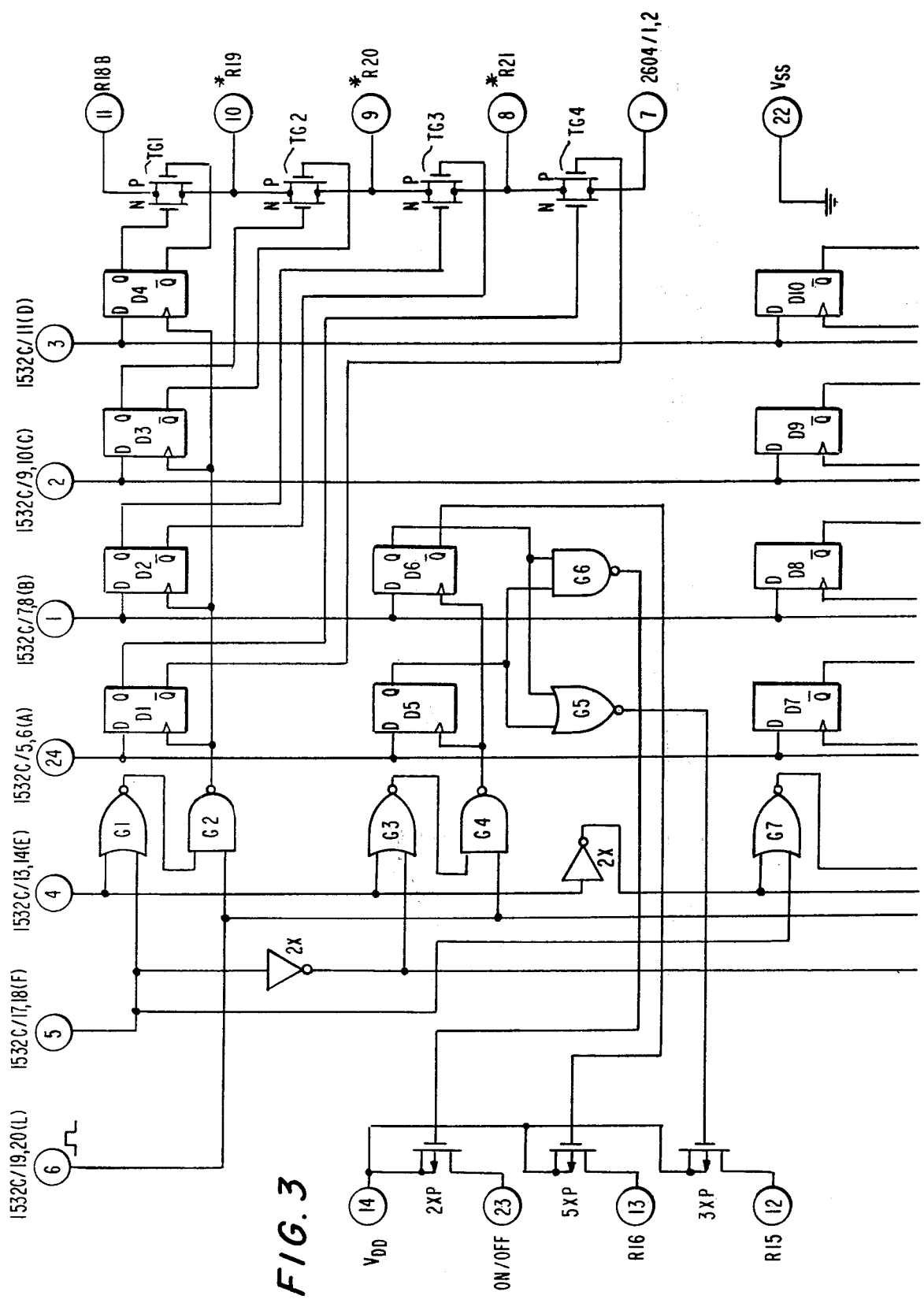
Figure 4:
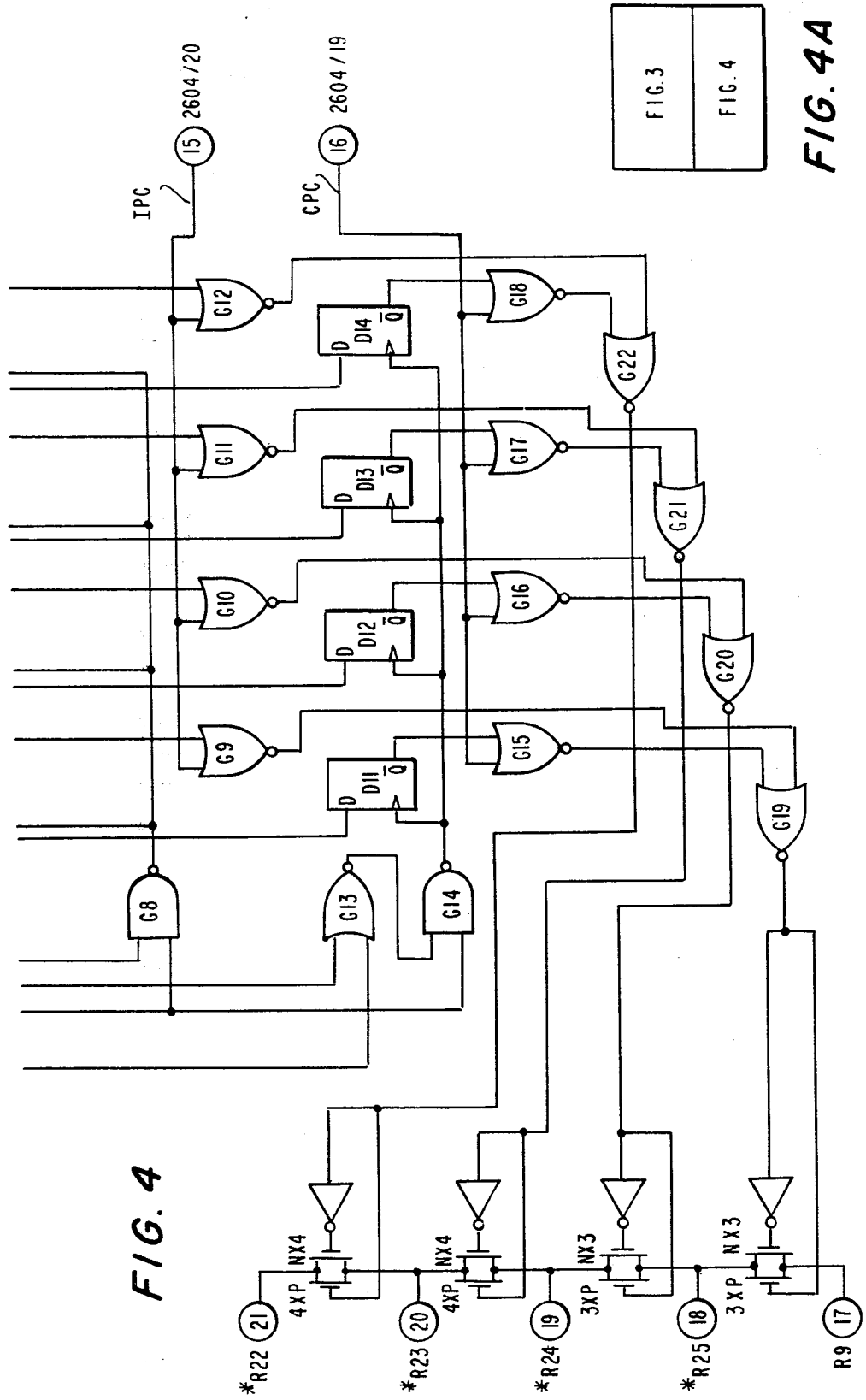
Figure 5:
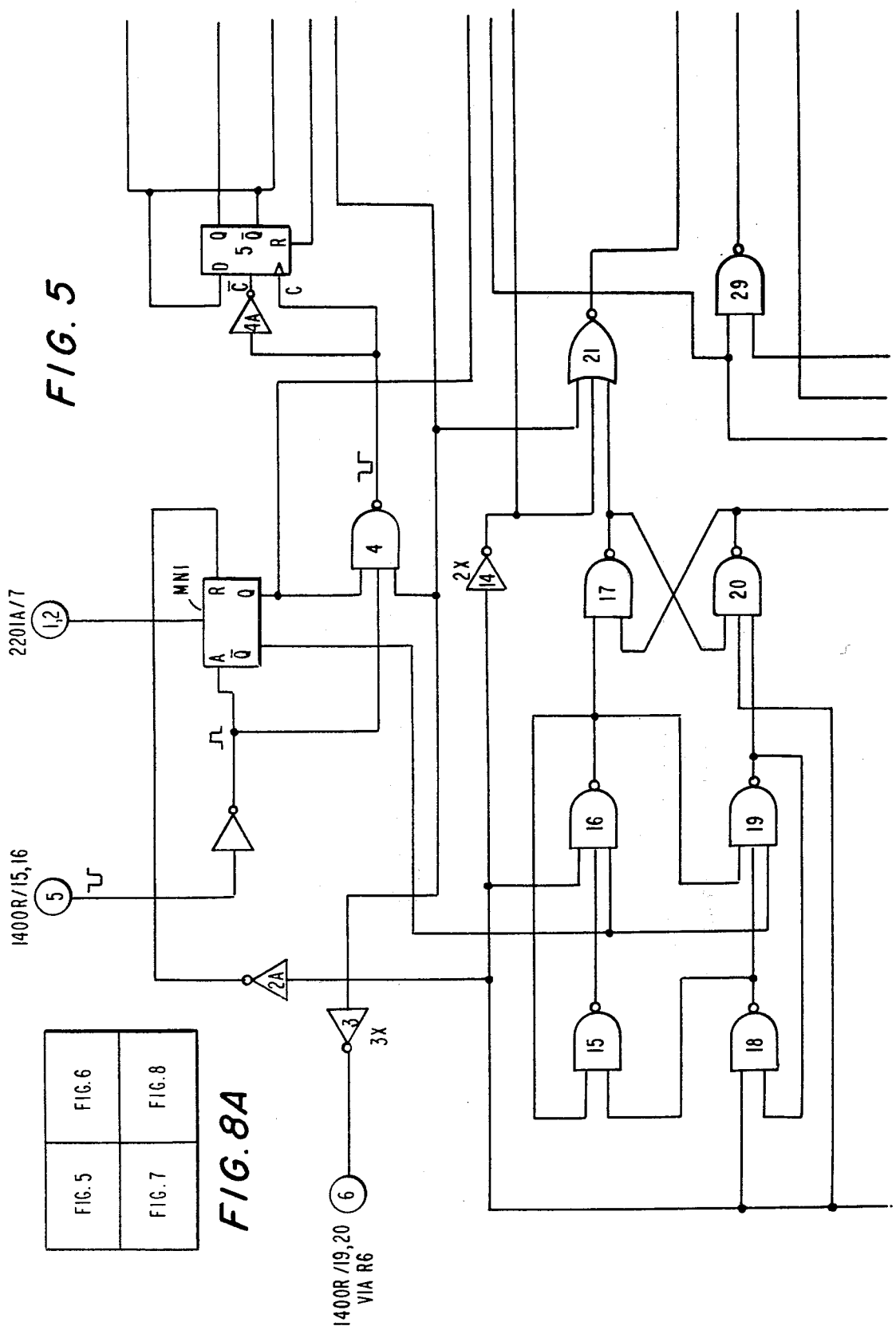
Figure 6:
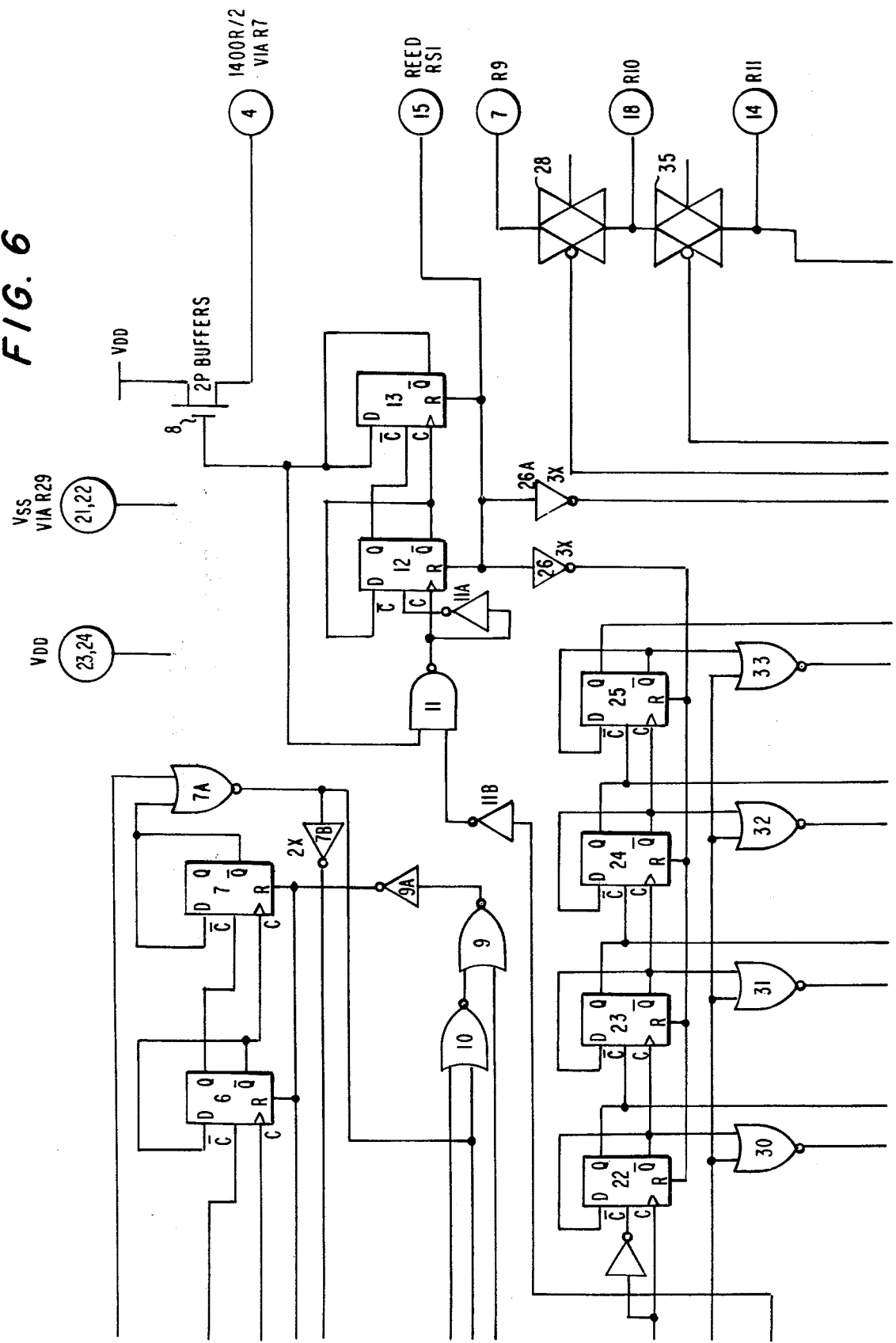
Figure 7:
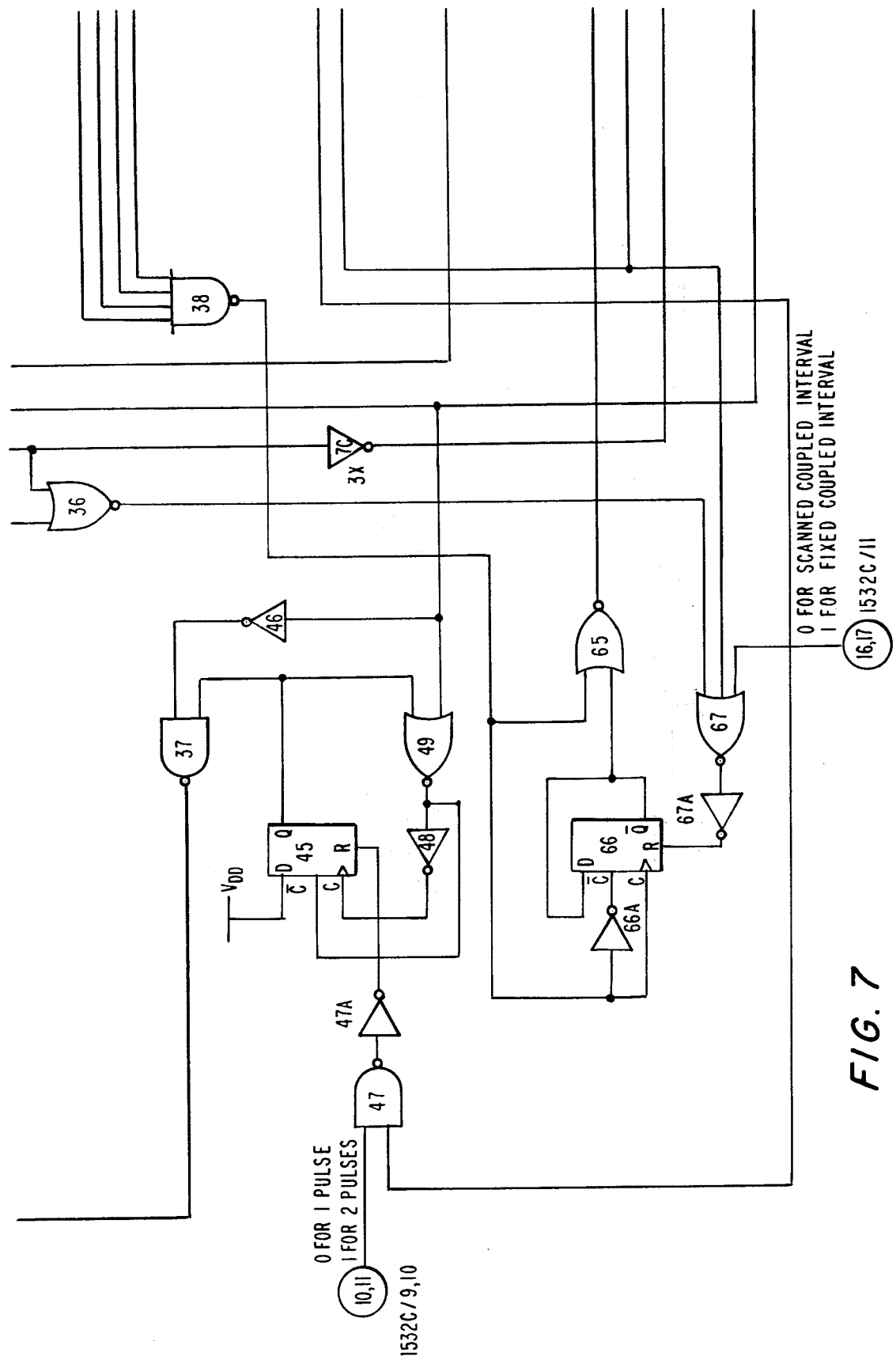
Figure 8:
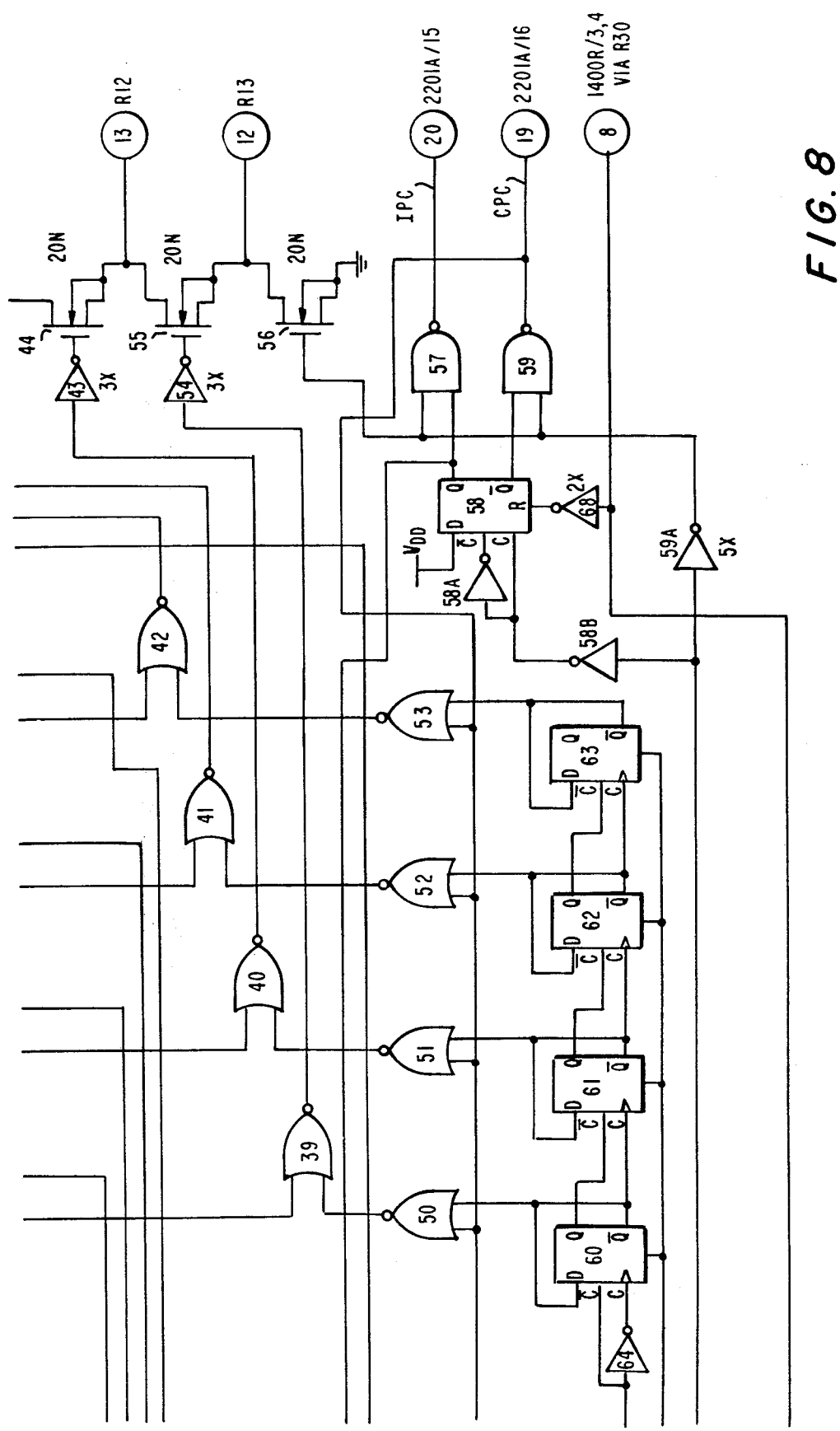
Figure 9:
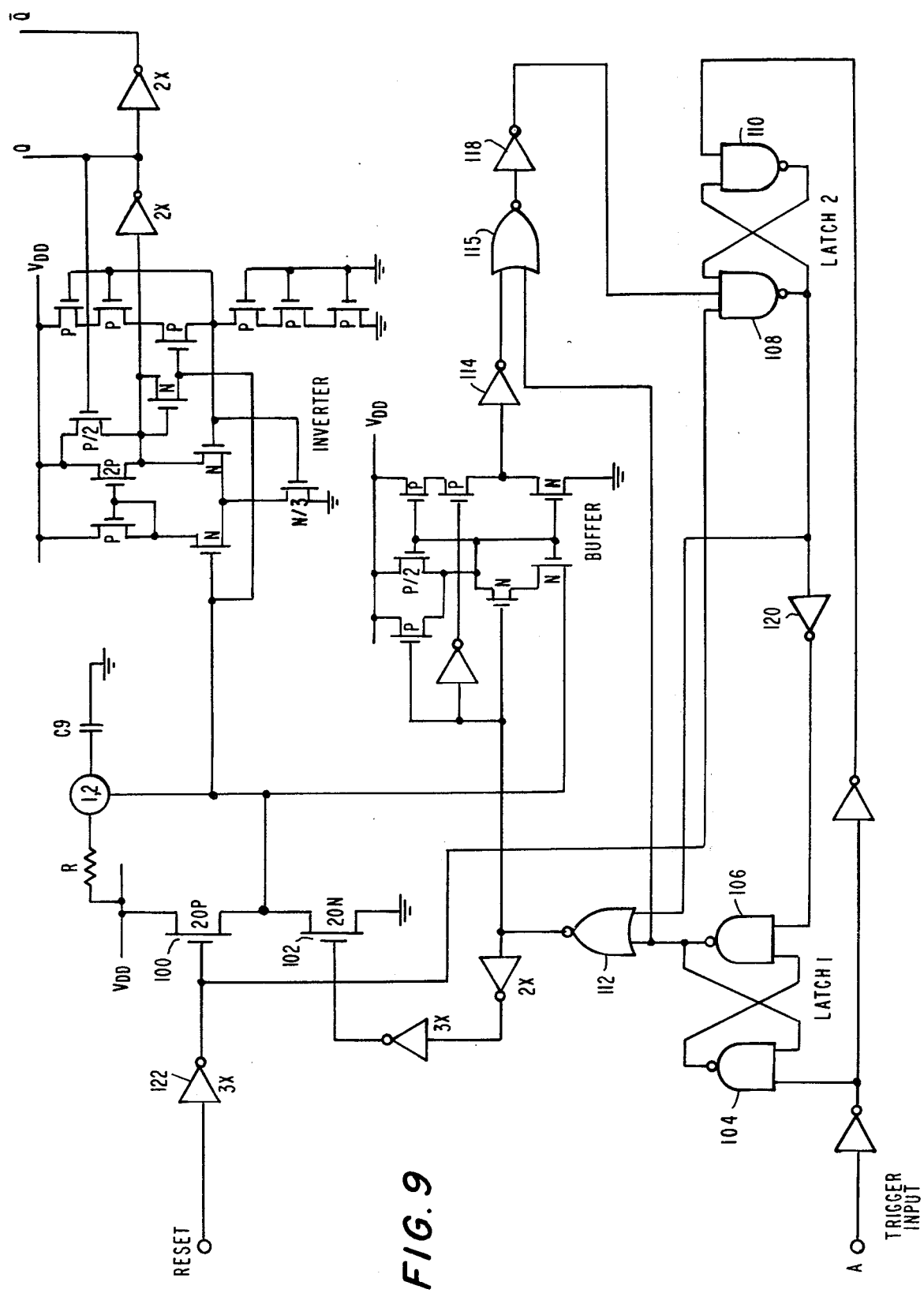
Figure 10:
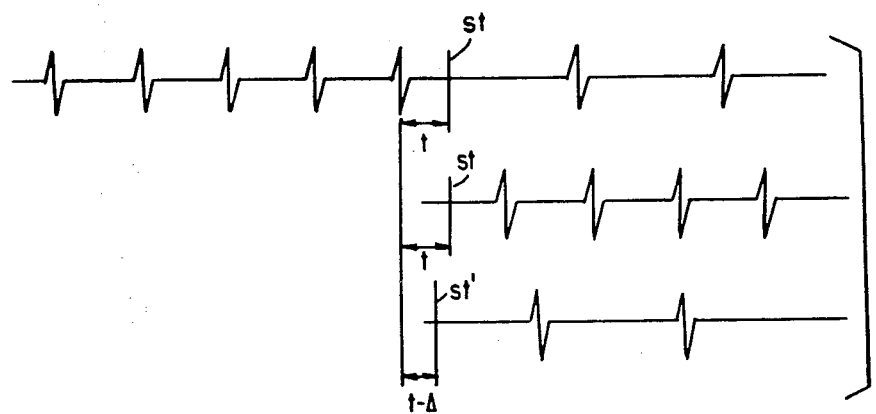
Figure 11:
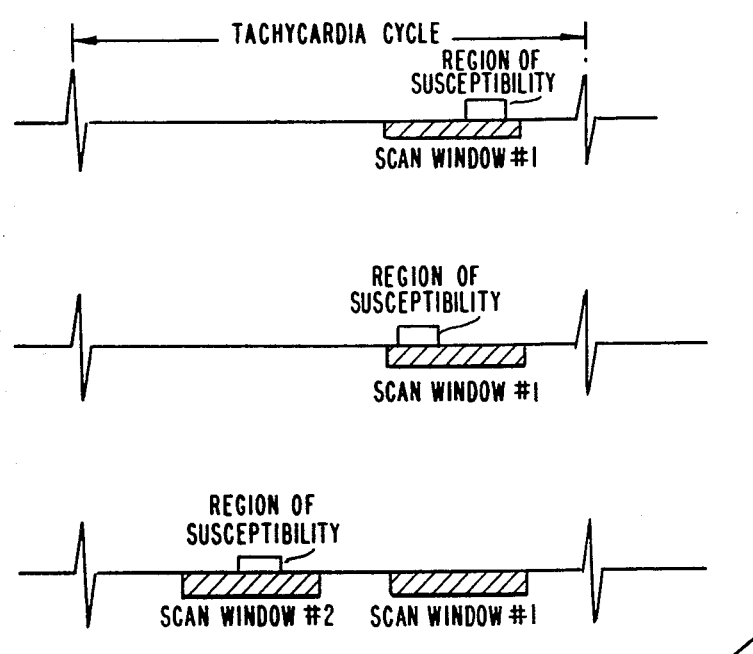
Figure 13:
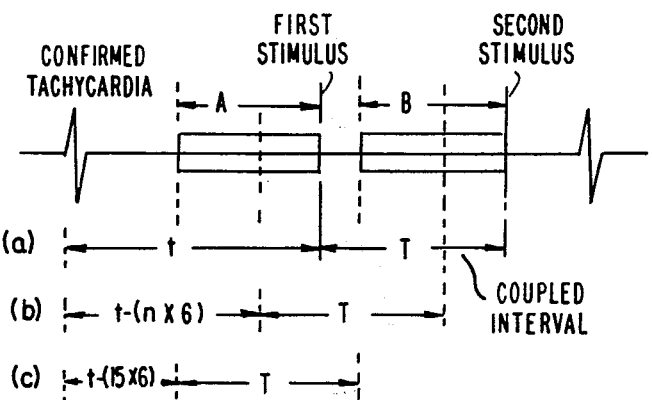
Figure 14:
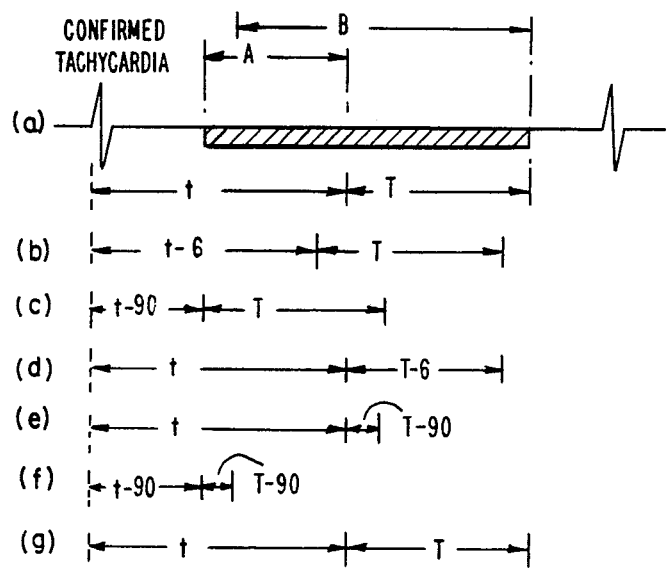
Figure 15:
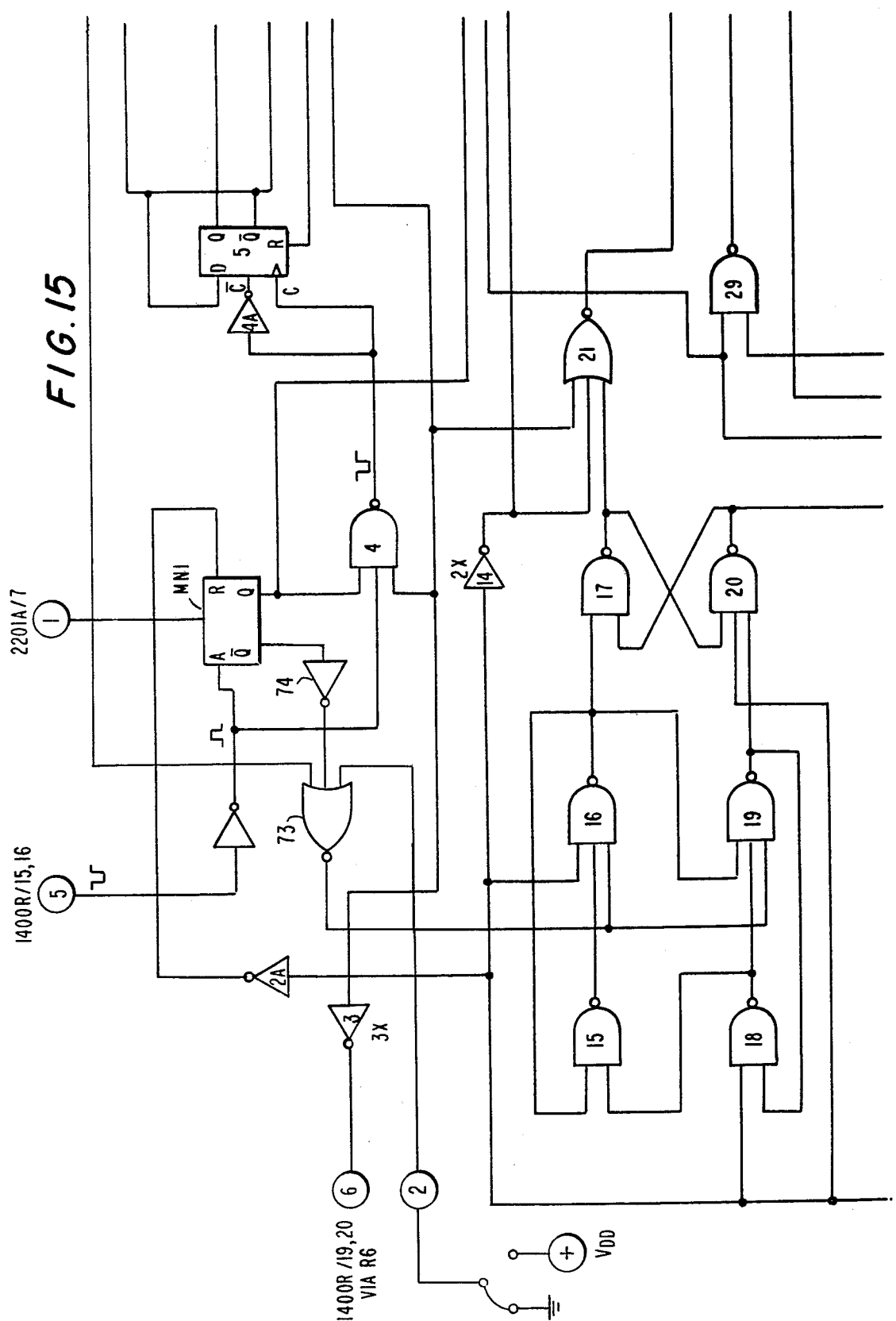
Figure 16:
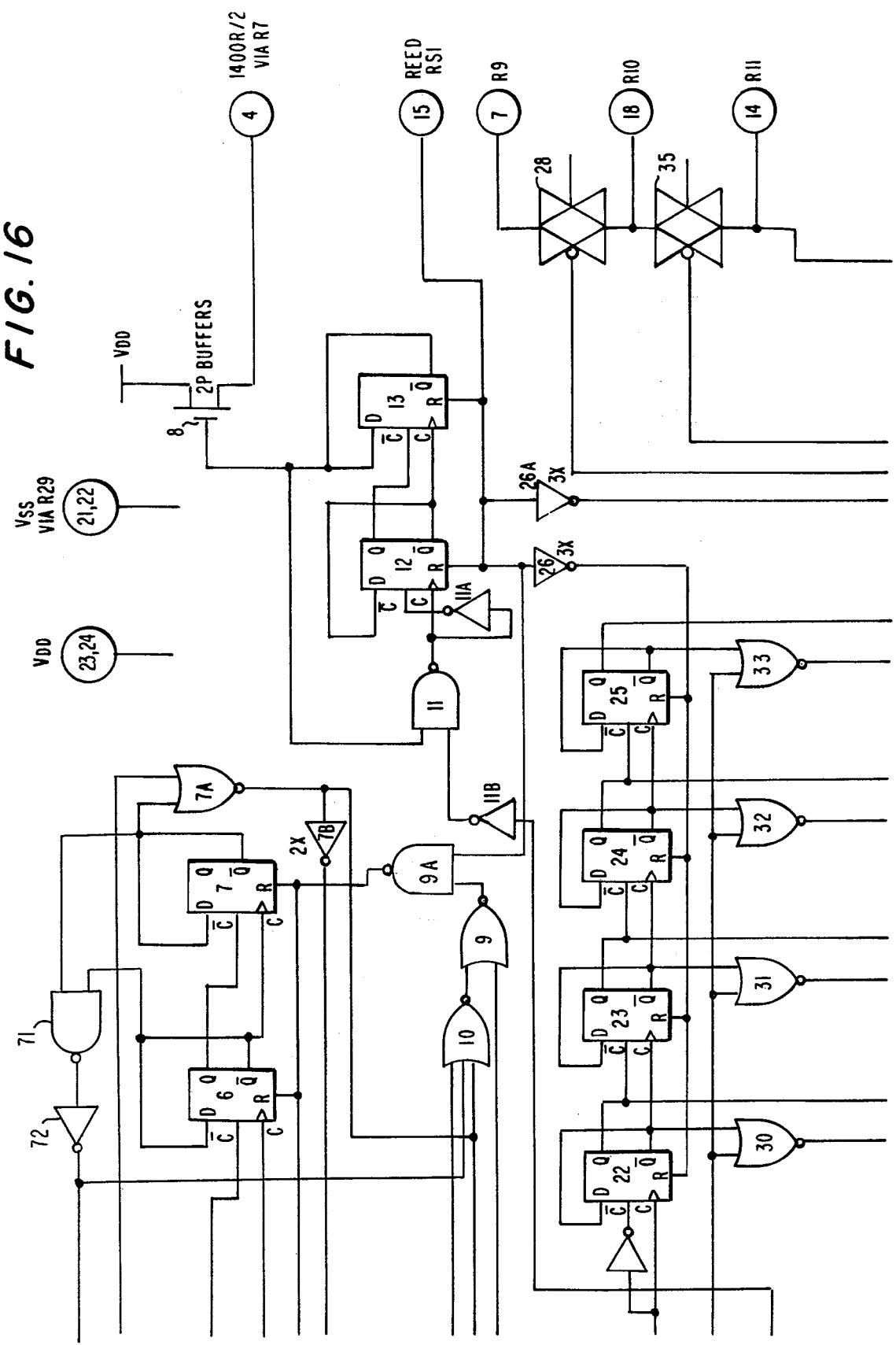

Further objects, features and advantages of our invention will become apparent upon consideration of the following detailed description in conjunction with the drawing, in which:

FIGS. 1–14 are identical to the same-numbered figures in our copending application, with FIGS. 1 and 2, arranged as shown in FIG. 2A, depicting the five chips used in the pacer, their interconnections, and the discrete components included in the circuit;

FIGS. 3 and 4, arranged as shown in FIG. 4A, depicting the circuitry contained in chip IC4 of FIG. 2;

FIGS. 5–8, arranged as shown in FIG. 8A, depicting the circuitry contained in chip IC3 of FIG. 2;

FIG. 9 depicting the details of monostable multivibrator MN1 which is shown only in block form in FIG. 5; and FIGS. 10–14 depicting timing waveforms which facilitate an understanding of the pacer operation; and FIGS. 15 and 16, with FIG. 15 being placed to the left of FIG. 16, depict the modifications required in the circuitry shown on FIGS. 5 and 6 (part of chip IC3) in accordance with the principles of our present invention and in the illustrative embodiment thereof.

We will not herein repeat the detailed description of our copending application. Instead, the emphasis will be on FIGS. 5 and 6 of our copending application and the changes made thereto which are depicted in FIGS. 15 and 16. The timing waveforms of FIGS. 10–14, for example, will not be described in detail; those skilled in the art will appreciate how they characterize the pacer operation, especially in view of the general description presented above. The timing waveforms are included in the drawing for the sake of completeness and because the waveforms themselves characterize for those skilled in the art the pacer operation.

THE PACER OF FIGS. 1–9

Of the five chips IC1–IC5 shown on FIGS. 1 and 2, chip IC3 is the most complicated and the details of this chip are depicted in FIGS. 5–8. One of the elements on the chip is multivibrator MN1 on FIG. 5, shown in detail in FIG. 9. All that is required for an understanding of the present invention is to appreciate the relationships between the input and output signals associated with the multivibrator. The multivibrator is a re-triggerable device which generates a positive pulse at its Q output each time that a positive trigger, indictive of a heartbeat, is received at the A input. If another trigger is received before the multivibrator has timed out, the Q output remains high for another timing period. A positive potential at the reset (R) input resets the multivibrator with the Q output returning to its normally low potential and the $\overline{Q}$ output returning to its normally high potential. The duration of each pulse following receipt of a positive trigger pulse at the A input is controlled by various components connected to pins 1 and 2 on chip IC3. These two shorted pins are connected to both capacitor C9 on FIG. 2 and a resistor chain, the first resistor of which is R21 as shown on FIG. 2. Some of the resistors in the chain are shorted depending on how the pacer has been programmed. But the total impedance determines the programmed "tachy rate", that is, the minimum inter-beat interval which, if exceeded, will abort a tachycardia confirmation cycle.

Referring to the overall system as shown on FIGS. 1 and 2, chips IC1, IC2 and IC5 are standard-type chips used in heart pacers; they will be described below only in terms of their input and output signals, and the functions which they perform. Chips IC3 and IC4 are specially-designed chips and they are depicted in detail.

Each of the five chips on FIGS. 1 and 2 is designated not only by one of the labels IC1–IC5, but also by its chip number, e.g., chip IC5 bears number 1532C. On each of the two sets of chip drawings of FIGS. 3 and 4, and FIGS. 5–8, each pin of the respective chip is labeled not only by number, but also by its connection in the overall system. For example, pin 5 of chip IC3 (see FIG. 5) has adjacent to it the designation 1400R/15,16. This means that pin 5 of chip IC3 is connected to pins 15 and 16 of chip IC2 (1400R). Referring to FIGS. 1 and 2, it will be seen that pin 5 of chip IC3 is indeed connected to pins 15 and 16 of chip IC2. As another example, pin 21 of chip IC4 (see FIG. 4) bears the designation *R22. This means that pin 21 of the chip is connected to resistor *R22, as shown in FIG. 2.

In FIGS. 1 and 2, it will be noted that several of the resistors have an asterisk preceding their labels; this symbol identifies a resistor as being a high-stability component. Several of the resistors are not provided with component values, and instead are labeled "SOT". Such a designation refers to the fact that the value of the respective component is "selected on test", i.e., a component value is selected which provides proper operation. The component ranges for the resistors designated as SOT are as follows:

R13:8.06–11.5M
R8:220–420K
R17:4.81–8.66M
R18B:8.2–11.5M
R27:1.2–2.4M
R15:3.9–6.8M

It will also be noted that many of the inputs and outputs of the chips of FIGS. 1 and 2 have two pin designations. For example, chip IC2 on FIG. 1 is connected to the positive supply rail via two pins 23, 24. It is standard practice in the pacer art to provide such double connections for increased reliability; even if one pin connection fails, because the two pins are internally connected on the chip, the chip still functions for its intended purpose as long as the other pin connection remains intact.

Chip IC1 is a conventional sense amplifier/comparator, and chip IC2 is a conventional timing oscillator/pulse doubler; both chips are standard chips used in the manufacture of heart pacers and are available from Amalgamated Wireless Microelectronics Pty. Ltd. of Sydney, Australia. Chip IC4 serves primarily to store programmed values and to control the shorting out of selected resistors in two resistor chains. Chip IC5, used by Telectronics Pty. Ltd. in its standard line of heart pacers, is a standard-type "program controller" chip; this chip detects reed closures, as controlled by an external programmer, and sets programmable parameters accordingly in the pacer. Techniques for programming pacers are standard in the industry, the design of program controllers is well known in the art, and there is nothing unique abut use of the particular chip No. 1532C insofar as the present invention is concerned; any conventional programming technique may be employed, as long as it provides the signals to be described below.

Reed switch RS1 on FIG. 1 is connected to pins 15,16 of chip IC5, with resistor R26 serving as the pull-up for the switch. Under the influence of an external magnetic field, the normally-open reed switch is closed, and a ground potential is applied to pins 15,16. Resistor R27 and capacitor C11 are the timing components for an internal oscillator on the chip. Incoming reed pulses must be properly timed if an incoming programming sequence is to be treated as valid; the internal oscillator on the chip determines whether valid programming pulses are received. For example, if the reed switch is held closed for a long time period by placing an external magnet over the chest of the patient, because the resulting pulse at pins 15,16 is too long relative to the oscillator timing, the reed closure has no effect on the outputs of chip IC5.

There are six parameters which may be programmed. The first is pulse width, i.e., the width of each pulse generated by the pacer. Two bits are used to represent the pulse width, and there are thus four possible values. The first value is 0—effectively disabling the pacer since no pulses are generated. The three pulse widths which can be controlled when the pacer is operative are 0.25, 0.35 and 0.6 milliseconds.

The second parameter is sensitivity. A single bit is used to control sensitivity of the sense amplifier/comparator chip IC1, as is standard in the pacer art. The two sensitivities are 1 millivolt and 2 millivolts.

Figure 12:
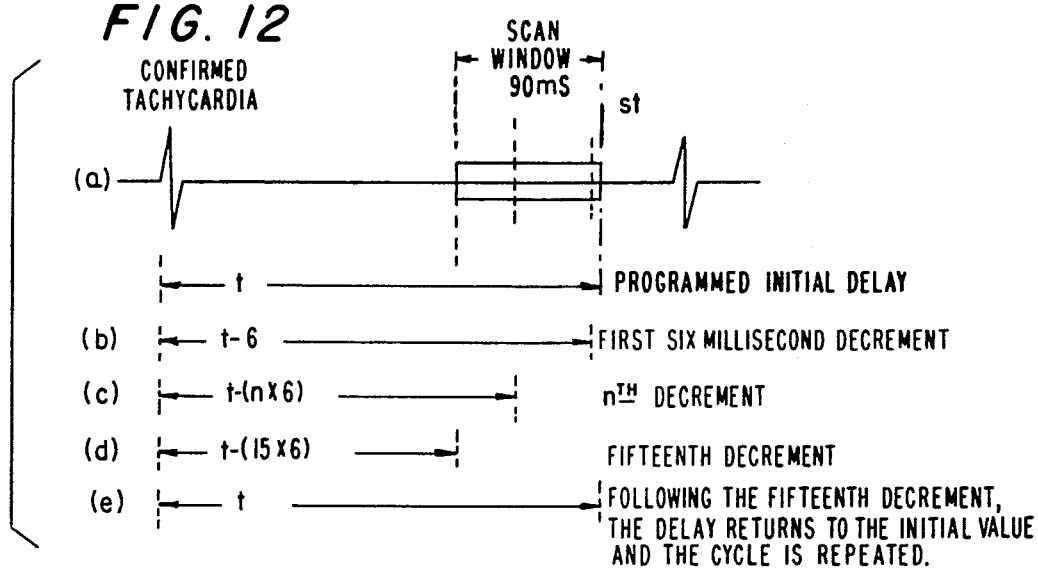

The third programmed parameter pertains to the second stimulus which is generated during each pacing cycle. As depicted in FIG. 12, in some cases it may be desired not to have a second stimulus at all. As depicted in FIG. 13, in some cases it may be desired to have a second stimulus which always follows the first stimulus by a fixed (programmed) coupled interval. Finally, as depicted in FIG. 14, in other cases it may be desired to have a second stimulus which follows a coupled interval which is scanned (the maximum coupled interval being programmed). One bit is required to represent whether a second stimulus is generated at all. If it is, another bit represents whether the coupled interval is fixed or scanned.

The fourth parameter is the maximum initial delay value, shown by the letter t on FIGS. 12–14. Scanning of the initial delay begins with this value the first time that the pacer is called upon to terminate tachycardia after the initial programming. (Thereafter, the successful initial delay is retained, and subsequent scanning begins with the retained value.) There are 12 maximum initial delay values from which the physician can choose, and thus four bits are required to represent them. The values are 200, 210, 230, 250, 270, 290, 300, 320, 340, 360, 380 and 390 milliseconds.

The fifth parameter which can be programmed is the coupled interval, represented by the letter T in FIGS. 13 and 14. The programmed value serves no function if the pacer is programmed not to generate a second stimulus at all. But if the pacer is programmed to generate it, the programmed coupled interval represents either a fixed time (if the programming disables scanning of the coupled interval), or it represents the maximum coupled interval (if the programming calls for scanning of the coupled interval). In the latter case, the programmed coupled interval is the first value used when the pacer functions for the first time after the initial programming; thereafter, the scanning begins with the retained successful value. There are 15 coupled interval values from which the physician can choose, 125, 140, 160, 180, 200, 210, 230, 250, 270, 290, 300, 320, 340, 360 and 380 milliseconds, and thus four bits are required to represent them.

The sixth parameter which can be programmed is "tachy rate"; this is the parameter which determines the width of the pulse generated by monostable multivibrator MN1 (FIG. 9) each time that a heartbeat is detected. Four bits are used to represent the tachy rate, and the eight possible values are 40, 130, 140, 150, 165, 180, 200 and 225 beats per minute. For example, if a tachy rate of 150 beats per minute is selected, the pulse width of the multivibrator is adjusted such that the Q output of the multivibrator will remain high if, after any beat, four successive beats are detected at a rate which exceeds 150 beats per minute, with the inter-beat interval between any two successive beats not exceeding 60/150 or 400 milliseconds.

The program controller chip IC5 responds to incoming reed switch pulses in four programming steps, as described in our copending application. The outputs from chip IC5 are used to store data bits in various latches. The first programming step involves setting the tachy rate in flip-flops D1–D4 on FIG. 3. The second programming step involves storing the four bits which represent the initial delay in the latch which comprises register flip-flops D7–D10 on FIG. 3. In the third programming step, the four data bits which represent the coupled interval are latched into register flip-flops D11–D14 on FIG. 4. During the fourth programming step, all of the rest of the programming information is latched. The sensitivity of the sense amplifier/comparator chip IC1 is determined by a single bit which controls an external resistor connection to pin 12 of chip IC5. Pin 12 is coupled to the input filter circuit for chip IC1, and it directly controls the sensitivity of chip IC1 as is standard in the pacer art. The reason that the fourth programming step must always be the last one is that a separate latch is not provided for the sensitivity control. Chip IC5 itself serves as the sensitivity latch.

During the last programming step, the two pulse-width bits are stored in flip-flops D5 and D6 on FIG. 3. The last two pieces of information required by the pacer are two bits which represent whether a second stimulus is to be generated at all and, if it is, whether the coupled interval is to be fixed or scanned. These two data bits appear at the C and D outputs of programmer controller chip IC5, and chip IC5 itself serves as the latch for these bits just as it does for the sensitivity control.

In the description of monostable multivibrator MN1 (FIG. 9) above, it was explained that pins 1 and 2 of chip IC3 (see FIGS. 2 and 5) are connected to the junction of capacitor C9 and a resistor chain. The resistor chain is shown generally by the symbol R on FIG. 9, but actually comprises resistors R17, R18B, R18A, R19, R20 and R21 (see FIG. 2). The tachy-rate flip-flops D1–D4 on FIG. 3 have their Q and $\overline{Q}$ outputs connected to respective inputs of transmission gates TG1–TG4. Each gate, when turned on, shorts a pair of pins to each other, the five pins 7–11 being connected to the various resistors in the resistor chain just described. Thus if all of the transmission gates are off, all of the resistors are in the chain. On the other hand, when any two adjacent output pins are shorted to each other through a respective transmission gate, the resistor or resistors connected between the two pins are shorted and do not contribute to the total impedance. It is in this manner that the four tachy-rate flip-flops determine the minimum rate which must be exceeded for tachycardia confirmation, the physician being able to select from among eight different rates (one of which is "artificial" in that it is not really a legitimate tachy rate, but rather is programmed in order to attempt to induce tachycardia, as described in our copending application).

Referring to FIG. 2, there is an overall resistor chain comprising resistors R9–R13 and R22–R25. One or more of these resistors may be selectively shorted. The resistors and capacitor C8 on FIG. 1 control the timing of chip IC2, that is, when a stimulating pulse is generated. The same resistor chain is used to control the timing of both the first stimulus and the second stimulus (where required) and thus the same resistor chain determines both the initial delay and the coupled interval. It is chip IC3 which shorts out selected resistors from among those in the group R9–R13 to control scanning of both the initial delay and the coupled interval; as different pairs of pins among pins 12, 13, 14, 18 and 7 are shorted to each other during the scanning of both the initial delay and the coupled interval, both time periods decrease in 6-millisecond discrete steps. But the maximum time periods (when none of resistors R9–R13 are shorted) are controlled by chip IC4 and the selective shorting of resistors R22–R25. The circuitry on FIG. 4 (part of chip IC4) selectively shorts pairs of adjacent pins among pins 17–21 in order to control the maximum initial delay and the maximum coupled interval. The control is exercised by flip-flops D7–D10 or flip-flops D11–D14, depending upon whether it is the initial delay or the coupled interval which is to be timed. The same resistors are used for both types of control since the two types of timing come into play at different times during each cycle.

Chips IC1 and IC2 (1438B and 1400R) are commercially available devices and they perform standard functions. The two electrode connections (IND and STIM) are shown on the left side of FIG. 1. The indifferent electrode is grounded. The stimulating electrode is coupled both to pins 20,21 of chip IC1 and to pins 9,10 of chip IC2. Chip IC1 is a standard sense amplifier/comparator which serves to detect a heartbeat. As described above, the sensitivity is determined by program controller chip IC5 (pin 12). The components connected to chip IC1 are all standard, and the sense amplifier/comparator operation is the same as that to be found in prior art pacers. Whenever a heartbeat is detected, a positive pulse appears at output pins 9,10.

Chip IC2 is a timing oscillator. It is the "heart" of a conventional pacer, but is used in the illustrative embodiment of the invention only as a timer and pulse generator. A positive pulse appearing at pins 21, 22 is internally coupled through the chip to pins 19,20. The pulse is coupled through capacitor C6 to pins 17,18. A trigger input at pins 17,18 resets the internal oscillator in chip IC2 and starts a new timing cycle. Chip IC2 can operate in either the synchronous or the inhibit mode. In the former a stimulating pulse is generated at pins 9, 10 whenever a heartbeat is detected in order to reinforce it, and in the latter such a reinforcement pulse is not generated. Because pin 1 is grounded, chip IC2 operates in the inhibit mode.

If a positive potential is applied through resistor R6 to capacitor C6, the trigger pulses are not extended from pins 19,20 through the capacitor. Thus when pin 6 of chip IC3 (FIG. 2) is high, it inhibits the detection of heartbeats. A low potential applied to pins 17,18 also prevents the trigger inputs from resetting the timer. When reed switch RS1 is operated, the low potential applied through hot carrier diode D2 to pins 17,18 causes the oscillator in chip IC2 to run free and pacing pulses to be generated continuously. Pulses are in fact not generated continuously, however, but only as required under control of the remaining pacer circuitry.

Pacing pulses are generated at pins 9,10 of chip IC2, and are coupled through capacitor C5 to the stimulating electrode. Coincident with each pacing pulse, a negative pulse is generated at pins 3,4.

A negative pulse is also generated at pins 15,16 whenever a pacing pulse is delivered to the stimulating electrode, just as a negative pulse appears at pins 3,4. However, a negative pulse also appears at pins 15,16 whenever a heartbeat is detected, in which case a negative pulse does not appear at pins 3,4 since chip IC2 is operated in the inhibit mode. Capacitor C4 is the charge storage capacitor which discharges through pins 9,10 whenever a stimulating pulse is required. Capacitor C8, connected between pin pairs 15,16 and 13,14 is the rate timing capacitor. This capacitor, as well as resistor R8 and all of the resistors previously described in the resistor chain, determine the rate at which the internal oscillator of chip IC2 operates.

The potential at pins 11,12 of chip IC2 controls the width of each pulse which is generated, as described above.

Lastly, a high potential applied to pin 2 of chip IC2 disables the chip from generating pacing pulses at all. When pin 23 of chip IC4 (FIG. 2) is high in potential, the potential extended over the on/off conductor and through resistor R7 prevents pacing pulses from being generated. Capacitor C7 is normally charged through resistors R26, R4 so that it also normally inhibits pulse generation. Chip IC2 is thus held off most of the time. When a stimulus is required, capacitor C7 is discharged through diode D3 and resistor R31.

The system logic is controlled by chip IC3 (FIGS. 5-8). It is this circuitry, and especially that shown on FIGS. 5 and 6, which will be considered in the greatest detail inasmuch as the present invention involves changes in chip IC3.

When a heartbeat is detected, a negative pulse appears at pins 15,16 of chip IC2. This pulse is extended to pin 5 of chip IC3, as shown in FIGS. 1 and 2. The negative pulse is inverted and a positive pulse is applied to the trigger (A) input of the monostable multivibrator (FIG. 5). A positive pulse now appears at the Q output of the multivibrator, its duration being dependent upon the "tachy rate" programmed by the physician. The Q output is connected to one input of gate 4. The same pulse which triggers the multivibrator is applied to a second input of gate 4. The third gate input is connected to the output of inverter 7B which is normally high in potential. Thus as long as the output of inverter 7B is high, the output of gate 4 is pulsed low whenever a heartbeat is detected.

Flip-flops 5, 6 and 7 comprise a standard ripple counter which is initially reset to 000. With the $\overline{Q}$ output of each of flip-flops 5 and 7 initially high, and since they are connected to inputs of gate 7A, the gate output is low. The output is inverted by inverter 7B to apply a high potential to the third input of gate 4.

Flip-flop 5 is toggled on the railing edge of each output pulse from gate 4. If the counter is not reset, as successive heartbeats are detected and the counter cycles from 000 to 100, the $\overline{Q}$ output of at least one of flip-flops 5 and 7 remains high, and the output of gate 7A remains low. But when the fifth pulse is counted without the counter having been reset during the sequence, the $\overline{Q}$ output of each of flip-flops 5 and 7 is low, and the output of gate 7A goes high. The output of inverter 7B now goes low to disable gate 4; no further pulses are counted.

The Q output of multivibrator MN1 is connected to an input of gate 10. Whenever the multivibrator times out, that is, the Q output goes low without the output pulse being extended by the arrival of another trigger input before the time-out is over, one input to gate 10 goes low. The output of gate 7A is connected to the other input of gate 10, and this input is thus low in potential until five heartbeats have been counted. Thus each time-out of the multivibrator, as long as the counter has not reached a count of five, causes the output of gate 10 to go high.

One input of gate 9 is connected to the output of inverter 14, whose input is connected to the output of gate 37. The output of gate 37 is normally high, and thus one input to gate 9 is normally low. Consequently, whenever the Q output of the multivibrator goes low at the end of a time-out and the output of gate 10 goes high, the output of gate 9 goes low, and the output of inverter 9A goes high. Since the gate output is connected to the reset input of each flip-flop in the counter, this causes the three-stage counter to reset to 000.

Thus whenever a heartbeat occurs after a preceding heartbeat with an inter-beat interval longer than the reciprocal of the "tachy rate", the counter is reset and the tachycardia confirmation cycle starts all over again. But if five rapid heartbeats are detected in succession, the Q output of the multivibrator does not go low to reset the counter. Even though it may go low after the fifth beat is counted, the output of gate 7A is now high and it is connected to an input of gate 10; thus the output of inverter 9A is locked low as soon as a count of five is reached so that the counter cannot be reset even if the multivibrator times out.

The tachycardia confirmation test involves four rapid beats, not five, even though five beats are counted. The first beat merely serves as a time reference for the second. The basic test is whether four rapid beats occur in succession, each of which is too soon after the respective previous beat. Once tachycardia is confirmed, the counter remains at a count of five and further counting is inhibited. The low potential which is now at the output of inverter 7B holds gate 4 off.

The same potential is inverted by inverter 3 and thus a positive potential appears at pin 6 of chip IC3 (FIG. 5). As indicated on the left of FIG. 5, and as shown in FIGS. 1 and 2, the positive potential is extended through resistor R6 to pins 19,20 of chip IC2. Any further heartbeats which are detected by chip IC1 are thus ignored. Also, since the count of five was reached in the first place by a negative pulse appearing at pin 5 of chip IC3, which pulse resulted from chip IC2 having detected a heartbeat and generated a negative pulse at pins 15,16, the oscillator on chip IC2 generates a first stimulus. The reason for inhibiting heartbeat detection in chip IC2, by holding pins 19, 20 high as just described, is that the oscillator on chip IC2 is used to determine when the stimuli should be applied, and this timing function should not be interfered with by any heartbeats which may occur.

When the output of gate 7A first goes high, several things happen in addition to those described above. First, gate 29 is enabled since one of its inputs is now high. (Its other input, however, is still low.) Second, the positive potential is inverted by inverter 7C, and inverted once again by inverter 58B to clock flip-flop 58. Since the D input of the flip-flop is connected to the positive supply, the flip-flop is set and its Q output goes high to enable gate 57. Third, the positive potential which now appears at the output of inverter 59A is applied to the second input of gate 57 and also to the gate of transistor 56. The transistor turns on, and the output of gate 57 goes low.

The output of gate 57 is the IPC conductor which, as shown on FIG. 2, is extended from pin 20 of chip IC3 to pin 15 of chip IC4. When the IPC conductor goes low, chip IC4 (FIGS. 4 and 5) shorts out pre-selected ones of resistors R22-R25 for controlling the programmed (longest) initial delay. Capacitor C7 on FIG. 1 is initially charged to a positive potential, the positive potential at pin 2 of chip IC2 preventing the generation of stimulating pulses. Now that a stimulus is required, however, a low potential must be applied to pin 2 of chip IC2. Because conductor IPC is now low in potential, capacitor C7 discharges through diode D3 and resistor R31 so that a stimulus can be generated.

Referring to FIGS. 1 and 2 the overall resistor chain involved in all timing functions of chip IC2 consists of resistors R9-R13, R22-R25 and R8, different ones of the resistors being shorted out at different times. With transistor 56 on FIG. 8 now on, pin 12 of chip IC3 is grounded. As shown on FIG. 2, this shorts out resistor R13 from the resistor chain. The actual initial delay which is now tmied depends upon two sets of resistors, R9-R12 and R22-R25. The latter set is pre-selected and the same resistors are always placed in the chain whenever an initial delay is to be timed. If all of the resistors R9-R12 are included in the chain, then the pre-selected combination of resistors R22-R25 provides the longest initial delay, as programmed by the physician. But the actual initial delay in any cycle is determined by which of resistors R9-R12 happen to be shorted, i.e., how many 6-millisecond decrements have already taken place. Depending upon the total impedance of the resistor chain, the oscillator on chip IC2 times out and results in the generation of a first stimulating pulse. Coincident with this pulse, and as described above, a negative pulse is generated at pins 3,4 on chip IC2. This pulse is coupled through resistor R30 on FIG. 1 to pin 8 of chip IC3. As shown on FIG. 8, the negative pulse at pin 8 is inverted by inverter 68 and thus resets flip-flop 58. Gate 57 now turns off, and it is gate 59 whose CPC output now goes low.

When the CPC conductor goes low, a different combination of resistors R22-R25 is included in the resistor chain. Since the oscillator on chip IC2 is still free running as a result of pins 19,20 being held high (assuming that the second stimulus is to be generated), the coupled interval timing now takes place. Chip IC3 selects some other combination among resistors R9-R12 depending on how many decrements of the coupled interval have already taken place, as will be described below, but the resistors controlled by chip IC4 and the CPC signal (FIG. 4) are such that should all of resistors R9-R12 be included in the chain, the longest coupled interval will be timed. At the end of the interval, a second stimulus is generated.

Chip IC2 can generate a second pulse only if pin 2 is not held high to disable pulse generation. It is the IPC conductor going low which discharges capacitor C7 rapidly to permit the first pulse to be generated. Although the IPC conductor goes high when the CPC conductor goes low, capacitor C7 charges through the high-impedance resistor R4. The capacitor cannot charge fast enough to inhibit the generation of a second pulse even for a coupled interval of maximum duration.

Assuming that a second pulse is to be generated, pins 10,11 on FIG. 7 are high in potential. As soon as the Q output of flip-flop 58 goes high upon tachycardia confirmation, both inputs of gate 47 are high, its output goes low, and the output of inverter 47A goes high to reset flip-flop 45. The low potential at the Q output of the flip-flop disables gate 37, whose output remains high. The flip-flop output is initially high because the output of inverter 46 is low, the input to the inverter normally being held high by the high potential at pins 3,4 of chip IC2. Even though the negative input pulse at pin 8, which pulse is coincident with the first signals, is inverted by inverter 46 so that a positive pulse is applied to the other input of gate 37, the gate output remains high since flip-flop 45 is still reset.

The negative pulse at pin 8 is coupled to one input of gate 49. Since the other input to the gate is connected to the low Q output of flip-flop 45, the output of gate 49 goes high with the generation of the first stimulus. A negative pulse thus appears at the output of inverter 48, and flip-flop 45 is clocked on the trailing edge of the pulse; by this time flip-flop 58 has been reset so as to lift the reset from flip-flop 45. The Q output of flip-flop 45 thus goes high at the end of the pulse at pin 8, after the short switching time of the flip-flop. Although one input of gate 37 is thus now held high, the output of inverter 46 is low once again since the pulse at pin 8 has terminated. Thus the first stimulus results in the setting of flip-flop 45 but the output of gate 37 remains high.

The pulse at pin 8 which is coincident which the second stimulus has no effect on flip-flop 45, the flip-flop remaining set until the next tachycardia confirmation at which time flip-flop 58 is set once again and gate 47 causes flip-flop 45 to reset. But the second pulse at pin 8, through inverter 46, causes the output of gate 37 to now go low and the output of inverter 14 to go high. The output of gate 9 thus goes low and the output of inverter 9A goes high in order to reset the ripple counter which comprises flip-flops 5-7. Since two pulses have been delivered, the system now starts looking for a tachycardia episode all over again, in order to determine whether another pair of pulses must be generated. Toward this end, monostable multivibrator MN1 is reset by the negative pulse at the output of gate 37, after inversion by inverter 2A.

If only a single stimulus is to be generated, pins 10,11 on FIG. 7 are low. Consequently, the output of gate 47 is high and the output of inverter 47A is low so that flip-flop 45 is not reset by the setting of flip-flop 58. The Q output of flip-flop 45 remains permanently high. The first negative pulse at pin 8, which pulse is coincident with the first stimulus, results in the output of gate 37 going low. The 3-bit counter comprising flip-flops 5–7 is thus reset after the first stimulus is generated. Flip-flop 58 is also reset by the first negative pulse at pin 8 and its $\overline{Q}$ output goes high to enable one input of gate 59. However, the other input is derived from the output of gate 7A which now goes low once again with the resetting of flip-flops 5 and 7. Consequently, even though flip-flop 58 is reset, the output of gate 59 does not go low; the CPC conductor remains high and there is no timing of a coupled interval.

Reed switch RS1 on FIG. 1 is connected to pin 15 of chip IC3. Referring to FIG. 6, it will be noted that each time the reed switch is operated and a ground potential appears at pin 15, inverters 26 and 26A apply positive reset pulses to all of flip-flops 22–25 and 60–63. As will be described below, these are the flip-flops which control the decrementing of the initial delay and the coupled interval by 6-millisecond decrements. During programming, each time the reed switch is operated all of the flip-flops are reset. This has the effect of inserting all of resistors R9–R12 (FIG. 2) in the resistor chain so that the longest (programmed) initial delay and coupled interval are first timed. Whenever a cycle does not result in tachycardia termination, flip-flops 22–25, which are arranged as a four-bit counter register, have their count incremented so that in the next cycle the initial delay is decremented by 6 milliseconds. After the fifteenth decrement, the initial delay is set to its highest value once again, as the counter cycles from 1111 to 0000. On alternate resettings of flip-flops 22–25, the similar counter register which comprises flip-flops 60–63 is incremented so that the coupled interval is decremented by 6 milliseconds.

It is gate 21 which controls the incrementing of the counter which comprises flip-flops 22–25. The count representing the number of 6-millisecond decrements of the initial delay is incremented whenever the output of gate 21 goes high. It is important that gate 21 not operate immediately after the one or two required stimuli are generated. That is because if tachycardia has been terminated, the count in flip-flops 22–25 should be retained so that the same initial delay and coupled interval values will be used when the next tachycardia episode is confirmed; downward scanning of the initial delay and the coupled interval always begin with the two last successful values. (It is only when a tachycardia episode is encountered following initial programming that the scanning begins with the maximum initial delay and the maximum coupled interval, since all of the flip-flops 22–25 and 60–63 are reset.)

Gates 15–20 comprise a standard D-type flip-flop. The output of gate 17 is the Q output of the flip-flop, and the output of gate 20 is the $\overline{Q}$ output. The set input, applied to inputs of gates 16 and 19, is derived from the $\overline{Q}$ output of multivibrator MN1, and the reset input is derived from the output of gate 37. The reason for the rather complicated form of flip-flop is that it must be set by the rising edge of the pulse at the $\overline{Q}$ output of the multivibrator, and the rising edge is not necessarily sharp; the flip-flop which is used, standard in the art, can be set even on a slowly rising edge.

The flip-flop is reset when the output of gate 37 goes low. This is after the first stimulus has been delivered if the pacer has been programmed not to deliver a second, or after the second stimulus has been delivered if the pacer has been programmed to deliver a second stimulus as well as a first. When the flip-flop resets, the Q output (output of gate 17) goes low, this output serving as one input to gate 21. The output of inverter 7B is connected to a second input of gate 21. This output is low during the initial delay and coupled interval timing periods, but when gate 37 controls the resetting of the flip-flop comprising gates 15–20, it also controls resetting of the counter comprising flip-flops 5–7. As soon as the latter flip-flops reset, the output of gate 7B goes high. Thus the output of gate 21 remains low even though the output of gate 17 no longer holds it low.

Gate 21 should not operate to increment the counter which comprises flip-flops 22–25 because when the tachycardia confirmation circuit is first enabled to operate once again, there is no way of knowing whether tachycardia has yet been terminated. If it has been terminated, the output of gate 21 should remain low so that flip-flop 22 is not toggled. In the event the output of gate 17 goes low before the output of inverter 7B goes high, two inputs to gate 21 would be low, and the output would go high to toggle flip-flop 22. In order to prevent this, the output of gate 37 is coupled through inverter 14 to a third input of gate 21. While the output of gate 37 is low the output of inverter 14 is high, so that the output of gate 21 remains low. By the time the output of gate 37 goes high once again, the output of inverter 7B has gone high so that it can hold the output of gate 21 low.

Thus by the time that the output of gate 37 reverts to its normally high state, the tachycardia confirmation circuit is enabled to operate once again, and the flip-flop which comprises gates 15–20 is reset with the output of gate 17 being low. If tachycardia has not been terminated, the multivibrator MN1 does not time out as it is continuously re-triggered by heartbeats which are once again detected (since pin 6 on FIG. 5 is now low), and the $\overline{Q}$ output remains low after the first multivibrator triggering. Consequently, following the next tachycardia confirmation, when the output of inverter 7B goes low, all three inputs to gate 21 are low in potential and the output goes high to clock flip-flop 22. Since tachycardia has not been terminated, the initial delay which is now timed is decremented by 6 milliseconds.

On the other hand, if tachycardia has been terminated, the multivibrator times out and the $\overline{Q}$ output goes high. The flip-flop comprising gates 15–20 is now set and the output of gate 17 goes high. Thus the output of gate 21 is held low. Even though another tachycardia episode may be confirmed some time later, when the output of inverter 7B goes low it does not result in the toggling of flip-flop 22. This allows the previously successful initial delay and coupled interval to be the first ones which are used.

It will be recalled that immediately upon tachycardia confirmation, the output of gate 7A goes high to enable one input of gate 29 (FIG. 5). The other input to this gate is connected to the output of gate 59, the CPC conductor, which is high in potential during the initial delay timing. Thus the output of gate 29 is low, and it enables the operation of each of gates 30–33. The outputs of these four gates are controlled by respective flip-flops 22–25, and the output of each of gates 30–33 is coupled to an input of a respective one of gates 39–42.

Each of these latter gates has another input, but these other inputs have no effect during the initial delay timing. The CPC conductor which is high in potential causes the output of each of gates 50–53 to remain low.

The outputs of gates 39–42 are coupled to respective transmission gates 28, 35, 44 and 55. As seen on FIG. 2, these are the four gates which control the selective shorting of resistors R9–R12 at pins 7, 18, 24 and 13 of chip IC3.

When flip-flops 22–25 represent a count of 0000, all of resistors R9–R12 are in the resistor chain. The resistors are weighted in the approximate ratio 1:2:4:8 so that as flip-flops 22–25 count in binary fashion, successive decrements of the initial delay are all the same.

Referring to FIG. 2, resistor R13 is shorted out by transistor 56 (FIG. 8) immediately upon tachycardia confirmation. Resistor R13 is nominally 10 M. In the absence of tachycardia, this artificially high resistor is placed in the resistor chain in order to make the time-out period of the oscillator in chip IC2 so high that no pacing pulses can be generated; even though pin 2 of chip IC2 is held high in the absence of tachycardia to prevent the generation of pacing pulses, chip IC2 also requires a resistive connection to pins 13,14. But when one or two stimuli must be generated, resistor R13 is removed from the circuit so that the only resistors which control initial delay and coupled interval timing are resistors R9–R12, R22–R25 and R8. The reason for providing resistor R8 is that if a minimum initial delay or coupled interval has been programmed, all of resistors R22–R25 are shorted out, and if all of resistors R9–R12 are similarly shorted out at the end of the scan of the initial delay or coupled interval, then there would be no resistance connected to pins 13,14 of chip IC2. Resistor R8 serves as the minimum resistance for controlling a minimum initial delay or minimum coupled interval when the counter which comprises flip-flops 22–25 or the counter which comprises flip-flops 60–63 counts all the way up to 1111 and shorts out all of resistors R9–R12.

If a second stimulus is to be provided, then as described above the CPC conductor (output of gate 59 on FIG. 8) goes low after the first stimulus is generated. The output of gate 29 is now high, the outputs of all of gates 30–33 are low, and thus flip-flops 22–25 have no effect on the outputs of gates 39–42. But because the CPC input to each of gates 50–53 is now low, the outputs of these gates are determined by the count contained in flip-flops 60–63. It is now these four flip-flops which determine which of resistors R9–R12 are included in the resistor chain for controlling the coupled interval.

Flip-flops 60–63 control the scanning of the coupled interval. The potential at pins 10,11 (FIG. 7) has already been described as controlling whether or not a second stimulus takes place at all. The description thus far has also taken into account the timing of the coupled interval in accordance with the count in flip-flops 60–63. There remains to consider how these flip-flops are cycled.

Cycling is not required at all if a fixed coupled interval is to be employed. In such a case, pins 16,17 (FIG. 7) are high in potential and the output of gate 67 is low. The output of gate 67A remains high to hold flip-flop 66 reset. Since the $\overline{Q}$ output of flip-flop is high, the output of gate 65 remains low. The output of gate 65 never exhibits a falling edge and flip-flop 60 is never toggled. All of flip-flops 60–63 are reset when the pacer is programmed. Consequently, all of resistors R9–R12 remain in the resistor chain during the coupled interval timing, and the coupled interval remains fixed at the programmed value. On the other hand, if the coupled interval is to be scanned, pins 16,17 are low in potential so that flip-flop 66 is not held reset and the output of gate 65 is not held low. The flip-flop is initially reset, however, following programming; the low potential at pin 15 (FIG. 6) when the reed switch closes is inverted by inverter 26A to control resetting the flip-flop 66 along with resetting of flip-flops 60–63.

In the presence of normal heartbeats, the output of gate 7A is low. Similarly, multivibrator MN1 keeps on timing out since heartbeats are occurring at a rate slower than the tachy rate; when the $\overline{Q}$ output of the multivibrator goes high at the end of each time-out, a set pulse is applied to the flip-flop comprising gates 15–20. The flip-flop is not reset because the output of gate 37 remains high, and thus the output of gate 20 remains low. Thus the output of gate 36 is high to enable an input of gate 67 so that flip-flop 66 remains reset.

Upon tachycardia confirmation, the output of gate 7A goes high and thus the output of gate 36 goes low so that the reset input of flip-flop 66 is no longer forced high. Assuming that tachycardia is not terminated, successive single pulses or successive double pulses are generated in successive cycles, and the output of gate 37 goes low at the end of each cycle. The flip-flop comprising gates 15–20 is continuously reset and, because the flip-flop is not set by the $\overline{Q}$ output of multivibrator MN1 going high, each time that the output of gate 7A goes high upon tachycardia confirmation gate 21 increments the count in flip-flops 22–25. The initial delay is scanned down to its minimum value, at which time flip-flops 22–25 represent a count of 1111. The four inputs of gate 38 are connected to the respective Q outputs of the four flip-flops, and at this time the output of the gate goes low. Although the output of gate 38 is coupled to one input of gate 65, the other input of gate 65 is connected to the $\overline{Q}$ output of flip-flop 66 which is high since the flip-flop is still reset. Consequently, the output of gate 65 still remains low.

If tachycardia is still not terminated, when the output of gate 7A next goes high gate 21 advances the count in flip-flops 22–25 from 1111 to 0000, and the output of gate 38 goes high once again. The positive step at the output of gate 38 clocks flip-flop 66 since it is applied directly to the C input and through inverter 66A to the $\overline{C}$ input. The flip-flop is now set and the $\overline{Q}$ output goes low. But the output of gate 65 still remains low since the output of gate 38 is now high. Consequently, another scan of the initial delay begins with the programmed value, without the count represented in flip-flops 60–63 being incremented.

During the last cycle of the next scan of the initial delay, however, when flip-flops 22–25 represent a count of 1111 and the output of gate 38 is low, both inputs to gate 65 are low and its output is high. If tachycardia is not terminated during this cycle, gate 7A goes high in the usual way upon the next tachycardia confirmation. As soon as flip-flops 22–25 are cycled frm 1111 to 0000 to begin a new scan of the initial delay, the output of gate 38 goes high once again and now the output of gate 65 goes low to exhibit a falling edge. This results in the clocking of flip-flop 60 and decrementing of the coupled interval by 6 milliseconds. When the output of gate 38 thus goes high for the second time, flip-flop 66 is clocked once again and it is now reset with the $\overline{Q}$ output going high. This holds the output of gate 65 low at the start of the next scan of the initial delay so that the coupled interval is not decremented even though gate 38 pulses once again. The net result is that the coupled interval is decremented by 6 milliseconds only at the start of every other scan of the initial delay.

The reason for this is that when the patient's heart has been beating normally but tachycardia is then confirmed, the scanning begins with the retained values of the initial delay and the coupled interval, stored in respective flip-flops 22–25 and 60–63. If tachycardia is not terminated, the initial delay is scanned down to the minimum value while the coupled interval remains at the previously successful value. Were the coupled interval to be decremented at the end of the first partial scan of the initial delay, there would be no scan of the higher value initial delays with the previously successful coupled interval. The first time that the maximum initial delay would be utilized at the start of the first complete scan, the coupled interval would be decremented and the previously successful value of the coupled interval would not be used at all until both the initial delay and the coupled interval would be scanned back to the point at which the coupled interval would be at the previously successful value. It is for this reason that the coupled interval is not decremented at the end of the scanning of the initial delay from the previously successful value to the minimum value. After this partial scan, a complete scan of the initial delay is controlled while using the previously successful coupled interval. It is only after this complete scan of the initial delay that the coupled interval is decremented.

The same operation ensues whether tachycardia is terminated during a scan of the initial delay which began with decrementing of the coupled interval, or during a scan of the initial delay at the beginning of which the coupled interval was not decremented. It makes no difference because upon tachycardia termination the output of gate 20 goes low while the output of gate 7A is low, and the output of gate 36 goes high to reset flip-flop 66.

It should be noted that the mechanism by which flip-flop 66 controls decrementing of the coupled interval only after every other complete scan of the initial delay is not really necessary during most of the cycling. It is only at the beginning of an overall scanning sequence that the coupled interval should not be decremented when flip-flops 22–25 are clocked to represent a count of 0000 for the first time. Thereafter, it is not necessary to control decrementing of the coupled interval only at the start of every other scan of the initial delay. It would be feasible, if desired, to allow the coupled interval to be decremented at the start of every scan of the initial delay, after there is at least one full scan of the initial delay with the previously successful coupled interval.

THE CHANGES DEPICTED IN FIGS. 15 AND 16

In order that the pacer of our invention, in the illustrative embodiment thereof, ignore the first inter-beat interval following the generation of a pacing pulse sequence, relatively few changes are necessary. The changes are as follows:

(1) At the top of FIG. 5, pins 1 and 2 on chip IC3 are both shown as being connected to pin 7 of chip IC4 (2201A). In FIG. 15, only pin 1 is shown as being connected to chip IC4 in this manner. Pin 2 of chip IC3 is ised for another purpose; an external strap serves to connect this pin either to ground or to the positive supply potential for the chip. In the usual case the pin is grounded, as shown in FIG. 15.

(2) In FIG. 5, the flip-flop comprising gates 15–20 is set by the $\overline{Q}$ output of multivibrator MN1 going high at the end of a time-out. In FIG. 15, however, the flip-flop is not set directly by the $\overline{Q}$ output of the multivibrator. Instead, the $\overline{Q}$ output is inverted by new inverter 74 and used as one input to new NOR gate 73. The flip-flop is set (so as to prevent decrementing of the previously used initial delay and coupled interval values following the next tachycardia confirmation) when the output of gate 73 goes high.

(3) New gates 71 and 72 on FIG. 16 serve to provide a high potential at the output of gate 72 only when the $\overline{Q}$ output of each of flip-flops 6 and 7 is high. The output of inverter 72 serves as an additional input to gate 10 on FIG. 16, and as an input to new gate 73 on FIG. 15.

(4) Although not specifically related to the present invention, inverter 9A on FIG. 6 has a NAND gate substituted for it on FIG. 16. The new input to the gate is connected to the read switch; this input is normally high so that the NAND gate functions as an inverter. The change is incorporated only so that closing of the reed switch will ensure that flip-flops 5, 6 and 7 are reset along with the other flip-flops controlled by the reed switch.

It is thus seen that the improved detection of tachycardia termination is controlled by only four additional gates 71–74, and the operation of the new circuitry will now be described.

A positive step at the output of gate 73 sets the flip-flop which comprises gates 15–20. It is the setting of the flip-flop which prevents incrementing of the count represented by flip-flops 22–25 following the next tachycardia confirmation. If pin 2 on FIGS. 15 is strapped to the positive supply, then one input of gate 73 is held high permanently and the output of the gate is permanently low; this prevents the flip-flop from being set and consequently every tachycardia confirmation results in incrementing of the count and scanning of the initial delay. This strap option may be selected in the event the "memory" function is not desired. It is also useful during testing of the assembly prior to final packaging in order to verify that the scanning sequence is as desired. But in the usual mode in which the pacer is operated, pin 2 is grounded and its effect on gate 73 can be ignored.

Following the generation of a pulse sequence, all of flip-flops 5–7 are reset and the $\overline{Q}$ outputs of flip-flops 6 and 7 are both high. Since these outputs are connected to respective inputs of gate 71, the output of this gate is low and the output of gate 72 is high. It will be recalled that the purpose of the changes in the circuit is to prevent the detection of the first inter-beat interval which follows a pacing sequence and which exceeds the reciprocal of the tachy rate from being interpreted as tachycardia termination. In such a case, the monostable multivibrator MN1 times out and its $\overline{Q}$ output, which is low during the timing period, goes high. The output of inverter 74 is thus pulsed high, with the output going low at the end of the time-out. Neglecting the input to gate 73 which is connected to the output of gate 72, when the output of gate 74 goes low at the end of the time-out, the output of gate 73 goes high to set the flip-flop comprising gates 15–20. This is the way in which the flip-flop is set when tachycardia is indeed terminated, that is, when a long inter-beat interval—other than the first one following a pacing sequence—is verified by the time-out of multivibrator MN1. But during the detection of the first two heartbeats, flip-flops 6 and 7 are both reset, flip-flop 6 being set only after flip-flop 5 switches from the one state to the zero state. Even if the multivibrator times out between the first two heartbeats, it does so while the output of gate 72 is still high. It is this high output which holds the output of gate 73 low even though the $\overline{Q}$ output of the multivibrator goes high at the termination of the time-out. Consequently, any time-out of the multivibrator between the first and second heartbeats following a pacing sequence cannot set the flip-flop which comprises gates 15–20; by not allowing the flip-flop to be set, when the counter comprising flip-flops 5–7 reaches a count of five subsequently (assuming that there is no intervening inter-beat interval following the second heartbeat which sets the flip-flop comprising gates 15–20), gate 21 will be pulsed in the usual way and the count in flip-flops 22–25 will be incremented.

When the second heartbeat is detected, flip-flop 6 is switched to the one state and the output of gate 72 goes low. Any subsequent time-out of the multivibrator, which indicates an inter-beat interval which exceeds the reciprocal of the tachy rate, results in the $\overline{Q}$ output of the multivibrator going high at the end of the time-out and the setting of the flip-flop comprising gates 15–20. This is the desired operation since tachycardia has been terminated.

The output of gate 72 is also extended to an input of gate 10. If the multivibrator times out after the first heartbeat is detected following a pacing sequence, its Q output returning to a low potential no longer resets the counter because the output of gate 10 is held low by the high potential at the output of gate 72. The counter can be reset only by a time-out which occurs following the detection of the second heartbeat at which time the output of gate 72 is low and has no effect on gate 10. What this means is that the counter always reaches a count of two following a pacing sequence, whether or not the inter-beat interval between the first two beats is longer than the reciprocal of the tachy rate. This, in turn, means that the counter will reach a count of five, indicating tachycardia confirmation, as long as there are three short inter-beat intervals following the second heartbeat. This is of no moment because three rapid heartbeats in succession are really just as good an indication of tachycardia as four rapid heartbeats in succession.

When a count of 010 is reached, the $\overline{Q}$ output of flip-flop 6 is low and holds the output of gate 72 low. Similar remarks apply to a count of 110 (decimal 3). When a count of 001 (decimal 4) is reached, the $\overline{Q}$ output of flip-flop 6 is high once again and can no longer hold the output of gate 72 low. But the $\overline{Q}$ output of flip-flop 7 is now low, and holds the output of gate 72 low so that the counter can be reset if there is a multivibrator time-out.

It should be appreciated that due to the circuit changes, tachycardia can be confirmed by counting three or four successive short inter-beat intervals. Following unsuccessful reversion, the first interval may be long or short; it makes no difference, however, because the counter is not reset. The next three short intervals result in the count incrementing up to five. Thus there may have been three or four successive short intervals, but even in the latter case it is the last three which matter.

Following a successful reversion, similar remarks apply. The counter always counts up to two before it can be reset by a third beat which follows the second by a long interval; it cannot be reset by a second beat even if it follows a first by a long interval. What this means is that if the counter has just been reset when tachycardia commences, then the counter will count four short intervals in cycling from a count of 1 to a count of 5. On the other hand, if tachycardia commences just after the second beat has been counted, only three short intervals are counted as the next three beats cycle the count from two to five.

It should be appreciated that if it is desired to "ignore" the inter-beat interval between the second and third heartbeats as well as the inter-beat interval between the first and second, a similar circuit may be provided for preventing the setting of the flip-flop comprising gates 15–20 until the multivibrator times out at some time following detection of the third heartbeat.

Although the invention has been described with reference to a particular embodiment, it is to be understood that this embodiment is merely illustrative of the application of the principles of the invention. For example, tachycardia termination could be determined only by sensing two or more multivibrator time-outs, provided that any time-out between the first two beats is ignored. Thus numerous modifications may be made in the illustrative embodiment of the invention and other arrangements may be devised without departing from the spirit and scope of the invention.

We claim:

1. A tachycardia control pacer comprising means for sensing a patient's heartbeats; means for confirming the presence of tachycardia dependent upon the rate at which heartbeats are sensed; means for applying at least one stimulating pulse to said patient's heart in an attempt to terminate tachycardia responsive to a tachycardia confirmation; and means for determining the termination of tachycardia dependent upon at least two successive sensed heartbeats, but excluding at least the first two which follow operation of said pulse applying means, being separated by a time interval greater than a predetermined minimum.

2. A tachycardia control pacer in accordance with claim 1 wherein said pulse applying means includes means for changing its timing from one cycle of operation to another unless its timing during the last cycle of operation was successful in terminating tachycardia.

3. A tachycardia control pacer in accordance with claim 2 wherein said tachycardia confirming means includes means for confirming the presence of tachycardia if at least a predetermined number of successive heartbeats are all separated by less than said predetermined minimum time interval.

4. A tachycardia control pacer in accordance with claim 3 wherein said tachycardia termination determining means includes means for excluding only the time interval between the first two sensed heartbeats following operation of said pulse applying means from affecting the determination of tachycardia termination.

5. A tachycardia control pacer in accordance with claim 1 wherein said tchycardia confirming means includes means for confirming the presence of tachycardia if at least a predetermined number of successive heartbeats are all separated by less than said predetermined minimum time interval.

6. A tachycardia control pacer in accordance with claim 1 wherein said tachycardia termination determining means includes means for excluding only the time interval between the first two sensed heartbeats following operation of said pulse applying means are excluded from affecting the operation of said tachycardia termination determining means.

7. A tachycardia control pacer comprising means for sensing a patient's heartbeats; means for confirming the presence of tachycardia dependent upon the rate at which heartbeats are sensed; means for generating and applying at least one stimulating pulse to said patient's heart in an attempt to terminate tachycardia responsive to a tachycardia confirmation; means for determining the termination of tachycardia dependent upon the rate at which heartbeats are sensed following operation of said pulse applying means; and means for inhibiting operation of said tachycardia termination determining means during a period of initial heart beating which immediately follows operation of said pulse applying means.

8. A tachycardia control pacer in accordance with claim 7 wherein said pulse generating and applying means includes means for changing its timing from one cycle of operation to another unless its timing during the last cycle of operation was successful in terminating tachycardia.

9. A tachycardia control pacer in accordance with claim 8 wherein said tachycardia confirming means includes means for confirming the presence of tachycardia if at least a predetermined number of successive heartbeats are all separated by less than a predetermined minimum time interval.

10. A tachycardia control pacer in accordance with claim 9 wherein said inhibiting means including means for controlling said period of initial heart beating extends up to at least the second beat which occurs following operation of said pulse applying means.

11. A tachycardia control pacer in accordance with claim 7 wherein said inhibiting said tachycardia confirming means includes means for confirming the presence of tachycardia if at least a predetermined number of successive heartbeats are all separated by less than a predetermined minimum time interval.

12. A tachycardia control pacer in accordance with claim 11 wherein said inhibiting means including means for controlling said period of initial heart beating extend up to at least the second beat which occurs following operation of said pulse generating and applying means.

13. A tachycardia control pcer in accordance with claim 7 wherein said inhibiting means including means for controlling said period of initial heart beating extend up to at least the second beat which occurs following operation of said pulse generating and applying means.

14. A tachycardia control pacer comprising means for confirming tachycardia; means responsive to said confirming means for generating a pair of heart-stimulating pulses, the first of said pulses being generated at the end of an initial delay which follows operation of said confirming means, and the second of said pulses being generated at the end of a coupled interval which follows said first pulse; means for scanning both said initial delay and said coupled interval during successive cycles of operation of said pulse generating means, and for retaining the last-used values of initial delay and coupled interval; and means for detecting a normal heartbeat which occurs after a predetermined time interval which follows the preceding heartbeat to indicate tachycardia termination; said scanning means operating to change the value of at least one of said initial delay and said coupled interval following tachycardia confirmation when said first and second pulses are generated, and said normal heartbeat detecting means operating to inhibit any changes by said scanning means during the next cycle of operation of said pulse generating means following the next tachycardia confirmation; characterized by means for preventing operation of said normal heartbeat detecting means until after at least two heartbeats have occurred following operation of said pulse generating means.

15. A tachycardia control pacer comprising means for confirming tachycardia; means responsive to said confirming means for generating at least one heart stimulating pulse at the end of a delay which follows operation of said confirming means; means for scanning said delay during successive cycles of operation of said pulse generating means, and for retaining the last-used value of said delay; and means for detecting a normal heartbeat which occurs after a predetermined time interval which follows the preceding heartbeat to indicate tachycardia termination; said scanning means operating to change the value of said delay following tachycardia confirmation, and said normal heartbeat detecting means operating to inhibit any changes by said scanning means during the next cycle of operation of said pulse generating means following the next tachycardia confirmation; characterized by means for preventing operation of said normal heartbeat detecting means until after at least two heartbeats have occurred following operation of said pulse generating means.

16. A tachycardia control pacer comprising means for confirming tachycardia; means responsive to said confirming means for generating at least one heart stimulating pulse at the end of a delay which follows operation of said confirming means; means for scanning said delay during on-going cycles of operation of said pulse generating means, and for retaining the last-used value of said delay; and means for determining the termination of tachycardia dependent upon the rate at which heartbeats occur following operation of said pulse generating means; said scanning means operating to change the value of said delay following tachycardia confirmation, and said tachycardia termination determining means operarting to inhibit any changes by said scanning means during the next cycle of operation of said pulse generating means following the next tachycardia confirmation; characterized by means for preventing operation of said tachycardia termination determining means during a period of initial heart beating which immediately follows operation of said pulse generating means.

17. A tachycardia control pacer in accordance with claim 16 wherein said inhibiting preventing means including means for controlling said period of initial heart beating extend up to at least the second beat which occurs following operation of said pulse generating and generating means.

18. A tachycardia control pacer comprising means for confirming tachycardia, means responsive to said confirming means for generating at least one timed heart-stimulating pulse within a time range which potentially allows tachycardia to be terminated, means for varying the timing of said pulse generating means during different cycles of operation of said pulse generating means, means for detecting tachycardia termination, and means for registering the last-used timing which was successful in terminating tachycardia for first use by said pulse generating means following the next tachycardia confirmation, characterized by said tachycardia termination detecting means operating to detect at least one heartbeat which follows the preceding heartbeat by at least a predetermined time interval provided said at least one heartbeat and the preceding heartbeat are not the first heartbeats to occur after operation of said pulse generating means.

* * * * *